US009950072B2

(12) United States Patent
Hanes et al.

(10) Patent No.: US 9,950,072 B2
(45) Date of Patent: *Apr. 24, 2018

(54) CONTROLLED RELEASE FORMULATIONS FOR THE DELIVERY OF HIF-1 INHIBITORS

(71) Applicant: The Johns Hopkins University, Baltimore, MD (US)

(72) Inventors: Justin Scot Hanes, Baltimore, MD (US); Peter Anthony Campochiaro, Baltimore, MD (US); Jie Fu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/599,853

(22) Filed: Jan. 19, 2015

(65) Prior Publication Data

US 2015/0141359 A1 May 21, 2015

Related U.S. Application Data

(63) Continuation of application No. 13/797,506, filed on Mar. 12, 2013, now Pat. No. 8,962,577.

(60) Provisional application No. 61/611,931, filed on Mar. 16, 2012.

(51) Int. Cl.
| | | |
|---|---|---|
| A61K 31/704 | (2006.01) | |
| A61K 9/14 | (2006.01) | |
| A61K 9/16 | (2006.01) | |
| A61K 47/50 | (2017.01) | |
| A61K 47/48 | (2006.01) | |
| A61K 9/00 | (2006.01) | |

(52) U.S. Cl.
CPC ...... *A61K 47/48215* (2013.01); *A61K 9/0048* (2013.01); *A61K 9/14* (2013.01); *A61K 9/16* (2013.01); *A61K 31/704* (2013.01); *A61K 47/488* (2013.01); *A61K 47/48192* (2013.01); *A61K 47/50* (2017.08)

(58) Field of Classification Search
None
See application file for complete search history.

(56) References Cited

U.S. PATENT DOCUMENTS

| | | | |
|---|---|---|---|
| 4,027,676 A | 6/1977 | Mattei | |
| 4,201,216 A | 5/1980 | Mattei | |
| 4,857,602 A | 8/1989 | Casey | |
| 4,994,074 A | 2/1991 | Bezwada | |
| 4,997,652 A | 3/1991 | Wong | |
| 5,412,072 A * | 5/1995 | Sakurai | A61K 47/48315 530/322 |
| 5,522,842 A | 6/1996 | Shalaby | |
| 5,540,930 A | 7/1996 | Guy | |
| 5,552,160 A | 9/1996 | Liversidge | |
| 5,567,435 A | 10/1996 | Hubbell | |
| 5,576,311 A | 11/1996 | Guy | |
| 5,578,325 A | 11/1996 | Domb | |
| 5,696,298 A | 12/1997 | Emanuele | |
| 5,710,135 A | 1/1998 | Leenders | |
| 5,869,130 A | 2/1999 | Ferrier | |
| 5,932,462 A | 8/1999 | Harris | |
| 6,007,845 A | 12/1999 | Domb | |
| 6,235,869 B1 | 5/2001 | Roby | |
| 6,270,806 B1 | 8/2001 | Liversidge | |
| 6,287,588 B1 | 9/2001 | Shih | |
| 6,413,539 B1 | 7/2002 | Shalaby | |
| 6,432,381 B2 | 8/2002 | Liversidge | |
| 6,495,164 B1 | 12/2002 | Ramstack | |
| 6,589,549 B2 | 7/2003 | Shih | |
| 6,706,289 B2 | 3/2004 | Lewis | |
| 7,550,154 B2 | 6/2009 | Saltzman | |
| 7,638,137 B2 | 12/2009 | Chauhan | |
| 7,645,736 B2 | 1/2010 | Bender | |
| 7,648,959 B2 | 1/2010 | Bender | |

(Continued)

FOREIGN PATENT DOCUMENTS

| | | |
|---|---|---|
| EP | 1752142 | 2/2007 |
| WO | 9207866 | 5/1992 |

(Continued)

OTHER PUBLICATIONS

Ben-Shaba et al, Macromol. Biosci. 2006, 6, 1019-1025.*
Gou et al., "Synthesis, self-assembly, and drug-loading capacity of well-defined cyclodextrin-centered drug-conjugated amphiphilic A 14 B 7 miktoarm star copolymers based on poly([epsilon]-cabrolactone) and Poly(ethylene glycol)", Biomacromolecules, 11(4): 934-43, 2010.*
Iwase et al., "Safe and effective polymeric-doxorubicin conjugate nanoparticles for prolonged antiagiogenic activity in the eye", Presetation abstract from presentation May 8, 2012; Program #3008/Poster # D857.*
Yang et al., "Biodegradable nanoparticles composed entirely of safe materials that rapidly penetrate human mucas", Agnew. Chem. Int. Ed., 50:1-5, (2011).*

(Continued)

Primary Examiner — Traviss C McIntosh, III
(74) Attorney, Agent, or Firm — Pabst Patent Group LLP

(57) ABSTRACT

Controlled release dosage formulations for the delivery of one or more HIF-1 inhibitors are provided. The controlled release formulations contain one or more HIF-1 inhibitors conjugated to or dispersed in a polymeric vehicle. The one or more HIF-1 inhibitors can be dispersed or encapsulated in a polymeric matrix. In some embodiments, the one or more HIF-1 inhibitors are covalently bound to a polymer, forming a polymer-drug conjugate. Polymeric vehicles can be formed into implants, microparticles, nanoparticles, or combinations thereof. Controlled release HIF-1 formulations provide prolonged therapeutic benefit while lowering side effects by releasing low levels of one or more HIF-1 inhibitors and/or HIF-1 inhibitor conjugates over a prolonged period of time. Controlled release dosage formulations can be used to treat or prevent a disease or disorder in a patient associated with vascularization, including cancer, obesity, and ocular diseases such as wet AMD.

54 Claims, 9 Drawing Sheets

(56) References Cited

U.S. PATENT DOCUMENTS

| | | | |
|---|---|---|---|
| 8,071,795 B2 | 12/2011 | VanMeir | |
| 8,354,476 B2 | 1/2013 | Hanes | |
| 8,394,799 B2 | 3/2013 | Lee | |
| 8,409,607 B2 | 4/2013 | Hughes | |
| 8,465,778 B2 | 6/2013 | Hughes | |
| 8,481,069 B2 | 7/2013 | Hughes | |
| 8,512,738 B2 | 8/2013 | Edelman | |
| 8,628,801 B2 | 1/2014 | Garreta | |
| 8,632,809 B2 | 1/2014 | Asgharian | |
| 8,663,674 B2 | 3/2014 | Wen | |
| 8,889,193 B2 | 11/2014 | McDonnell | |
| 8,911,768 B2 | 12/2014 | Whitcup | |
| 8,957,034 B2 | 2/2015 | Hanes | |
| 8,962,577 B2 * | 2/2015 | Hanes | A61K 47/48192 514/34 |
| 9,056,057 B2 | 6/2015 | Popov | |
| 2002/0035264 A1 | 3/2002 | Kararli | |
| 2003/0042137 A1 | 3/2003 | Mao | |
| 2004/0162580 A1 | 8/2004 | Hain | |
| 2004/0209806 A1 | 10/2004 | Rothenberg | |
| 2004/0209807 A1 | 10/2004 | Quay | |
| 2004/0234611 A1 | 11/2004 | Ahlheim | |
| 2004/0258763 A1 | 12/2004 | Bell | |
| 2005/0009910 A1 | 1/2005 | Hughes | |
| 2005/0070448 A1 | 3/2005 | Kupper | |
| 2005/0149118 A1 | 7/2005 | Koyfman | |
| 2005/0149119 A1 | 7/2005 | Koyfman | |
| 2007/0071756 A1 | 3/2007 | Peyman | |
| 2007/0087989 A1 | 4/2007 | Huang | |
| 2007/0093461 A1 | 4/2007 | Shafiee | |
| 2007/0141143 A1 | 6/2007 | Smithey | |
| 2007/0149593 A1 | 6/2007 | Ghosh | |
| 2007/0231360 A1 | 10/2007 | Peyman | |
| 2007/0238654 A1 | 10/2007 | Deschatelets | |
| 2007/0249536 A1 | 10/2007 | Ma | |
| 2008/0086199 A1 | 4/2008 | Dave | |
| 2008/0166411 A1 | 7/2008 | Shah | |
| 2008/0166414 A1 | 7/2008 | Hanes | |
| 2008/0268243 A1 | 10/2008 | Stopek | |
| 2008/0287341 A1 | 11/2008 | Chen | |
| 2008/0287990 A1 | 11/2008 | Smit | |
| 2008/0305172 A1 | 12/2008 | Ahlheim | |
| 2009/0011040 A1 | 1/2009 | Naash | |
| 2009/0060979 A1 | 3/2009 | Bezwada | |
| 2009/0087494 A1 | 4/2009 | Kompella | |
| 2009/0138041 A1 | 5/2009 | Stopek | |
| 2009/0203709 A1 | 8/2009 | Steinberg | |
| 2009/0220572 A1 | 9/2009 | Deschatelets | |
| 2009/0226531 A1 | 9/2009 | Lyons | |
| 2009/0234375 A1 | 9/2009 | Simon | |
| 2009/0247604 A1 | 10/2009 | Tang | |
| 2009/0291919 A1 | 11/2009 | Kaushal | |
| 2010/0034749 A1 | 2/2010 | Schulze | |
| 2010/0063135 A1 | 3/2010 | Dande | |
| 2010/0094340 A1 | 4/2010 | Stopek | |
| 2010/0152831 A1 | 6/2010 | Guo | |
| 2010/0209469 A1 | 8/2010 | Bezwada | |
| 2010/0215580 A1 | 8/2010 | Hanes | |
| 2010/0227905 A1 | 9/2010 | Kabra | |
| 2010/0247669 A1 | 9/2010 | Eliasof | |
| 2011/0264139 A1 | 10/2011 | Hunter | |
| 2012/0028910 A1 | 2/2012 | Combal | |
| 2012/0041481 A1 | 2/2012 | Daniloff | |
| 2012/0052041 A1 | 3/2012 | Basu | |
| 2012/0121661 A1 | 5/2012 | Schwartz | |
| 2012/0157499 A1 | 6/2012 | Hughes | |
| 2012/0201873 A1 | 8/2012 | Hohlbaum | |
| 2012/0245629 A1 | 9/2012 | Gross | |
| 2012/0269894 A1 | 10/2012 | Ahlheim | |
| 2012/0288464 A1 | 11/2012 | Carmichael | |
| 2012/0303010 A1 | 11/2012 | Vijfvinkel | |
| 2013/0041467 A1 | 2/2013 | Montenegro | |
| 2013/0071349 A1 | 3/2013 | Robinson | |
| 2013/0122064 A1 | 5/2013 | Ahlheim | |
| 2013/0164343 A1 | 6/2013 | Hanes | |
| 2013/0183244 A1 | 7/2013 | Hanes | |
| 2013/0217657 A1 | 8/2013 | Lindstrom | |
| 2013/0226234 A1 | 8/2013 | Avelar | |
| 2013/0236556 A1 | 9/2013 | Lai | |
| 2013/0272994 A1 | 10/2013 | Fu | |
| 2013/0274217 A1 | 10/2013 | Hanes | |
| 2013/0316001 A1 | 11/2013 | Popov | |
| 2013/0316006 A1 | 11/2013 | Popov | |
| 2013/0316009 A1 | 11/2013 | Popov | |
| 2013/0323313 A1 | 12/2013 | Suk | |
| 2014/0031408 A1 | 1/2014 | Edelman | |
| 2014/0107025 A1 | 4/2014 | Wirostko | |
| 2014/0178475 A1 | 6/2014 | Figueiredo | |
| 2014/0212661 A1 | 7/2014 | Khan | |
| 2014/0248358 A1 | 9/2014 | Figueiredo | |
| 2014/0249158 A1 | 9/2014 | Figueiredo | |
| 2014/0276482 A1 | 9/2014 | Astafieva | |
| 2014/0294986 A1 | 10/2014 | Liu | |
| 2014/0329913 A1 | 11/2014 | Hanes | |
| 2015/0044270 A1 | 2/2015 | McDonnell | |
| 2015/0086484 A1 | 3/2015 | Hanes | |
| 2015/0125539 A1 | 5/2015 | Popov | |
| 2015/0265542 A1 | 9/2015 | Popov | |
| 2015/0265543 A1 | 9/2015 | Popov | |
| 2015/0297531 A1 | 10/2015 | Ensign | |

FOREIGN PATENT DOCUMENTS

| | | |
|---|---|---|
| WO | 2007084418 | 5/1992 |
| WO | 2010132664 | 5/1992 |
| WO | 1995003356 | 2/1995 |
| WO | 9901498 | 1/1999 |
| WO | 0046147 | 8/2000 |
| WO | 2002038127 | 5/2002 |
| WO | 2004060977 | 7/2004 |
| WO | 005055985 | 6/2005 |
| WO | 2005072710 | 8/2005 |
| WO | 2010040188 | 6/2006 |
| WO | 2006109177 | 10/2006 |
| WO | 2006063249 | 2/2007 |
| WO | 2007016380 | 2/2007 |
| WO | 2013166408 | 7/2007 |
| WO | 2008030557 | 3/2008 |
| WO | 2013166436 | 4/2010 |
| WO | 2014047439 | 4/2010 |
| WO | 011080148 | 7/2011 |
| WO | 013110028 | 7/2013 |
| WO | 013138343 | 9/2013 |
| WO | 013138346 | 9/2013 |
| WO | 013166385 | 11/2013 |
| WO | 2013166498 | 11/2013 |

OTHER PUBLICATIONS

Yoshida et al., "Digoxin inhibits retinal ischemia-induced HIF-1 alpha expression and ocular neovascularization", Faseb J. 24:1759-1767, (2010).*

Ludwig, The use of mucoadhesive polymers in ocular drug delivery, Adv Drug Deliv Rev., 57:1595-639 (2005).

Memon, et al., "Optimization of formulation parameters on ocular loteprednol etabonate nanosuspension by media milling method", Int J Pharmacrut. Biol. Arch., 4:46-51 (2012).

Sahib, et al., "Solubilization of beclomethasone dipropionate in sterically stabilized phospholipid nanomicelles (SSMs):physicochemical and in vitro evaluations", Drug Des Dev Ther., 6:29-42 (2012).

Yang, et al., "Production of virus-mimetic mucus-penetrating particles for drug and gene delivery in mucosal tissues", Annual Meeting of AIChE Science and Engineering Forum, Nov. 16-21, Abstract 7058 (2008).

Erdmann and Uhrich, "Synthesis and degredation characteristics of salicylic acid-derived poly(anhydride-esters)" Biomaterials, 21:1941-6 (2000).

Grisanti and Ziemssen, "Bevacizumab: Off-labei uses in ophthalmology", Indian J Ophtalmol., 55(6):417-20 (2007).

Sagong, et al., "Intravitreal becacizumab for the treatment of neovascular glaucoma associated with central retinal artery occlusion", Koren J Ophthalmol., 23:215-8 (2009).

(56) References Cited

OTHER PUBLICATIONS

Jain and Kumar, "Self assembly of amphiphilic (PEG)(3)-PLA copolymer as polymersomes: preparation, characterization, and their evaluation as drug carrier", Biomacromolecules, 11:1027-35(2010).
Aich, et al., "Development of delivery methods for carbohyfrate-based drugs; controlled release of biologically-active shott chain fatty acid-hexosamine analogs" Glycoconj. J., 27(4):445-59 (2010).
Ben-Shabat, S. et al.,PEG-PLA block copolymer as potential drug carrier: preparation and characterization. Macromol. Biosci. 6:1019-1025 (2006).
Bourges, et al., "Pcular drug delivery targeting the retina and retinal pigment epithelium using polyactide nanoparticles", Inv Ophthalmology Vis Sci., 44(8):3562-9 (2003).
de Kozak, et al., "Intraocular injection of tamoxifen-loaded nanoparticles: a new treatment of experimental autoimmune uveoeretinitis", Eur. J Immunol., 34:3702-12 (2004).
Deosarkar, et al., "Polymeric particles conjugated with a ligand to VCAM-1 exhibit selective, avid, and focal ashesion to sites of atherosclerosis", Biotech. Bioeng., 101(2):400-7 (2008).
Desai, "Pluronic F127-based ocular delivery system containing biodegradable polyisobutylcyanoacrylate nanocapsules of pilocarpine", Drug Delivery, 7:201-7 (2000).
Dong, et al., "Vascular cell-adhesion molecule-1 plays a central role in he proangiogenic effects of oxidative stress", PNAS, 108(35):14614-9 (2011).
Escobar-Chavez, "Appilcation of thermo-reversible pluronic F-127 gels in pharmaceutical formulations", J Pharma Sci., 9(3):339-58 (2006).
Fiegel, et al., "Poly(ether-anhydride) dry powder aerosols for sustained drug delivery in the lungs", J Control Release, 96:411-23 (2004).
Giannavola, et al., "Influence of preparation conditions on Acyclovir-loaded poly-d, I-lactic acid nanospheres and effect of PEG coating on ocular drug bioavailability", Pharma. Res., 20(4):584-90 (2003).
Govender, et al., "PLGA nanoparticles prepared by nanoprecipitation: drug loading and release studies of a water soluble drug", J Cont. Rel., 57:171-85 (1999).
Kompella, et al., "Luteinizing hormone-releasing hormone agonist and transferrin functionalizations enhance nanoparticle delivery in a novel bovine ex vivo eye model", Mol. Vis., 12:1185-98 (2006).
Lai, et al., "Rapid transport of large polymeric nanopaticles in fresh undiluted human mucus",PNAS, 104(5):1482-7 (2007).
Newman, et al., "Uptake of poly(D,L-lactic-co-glycolic acid) microspheres by antigen-presenting cells in vivo", J Biomed Mater Res., 60(3):480-6 (2002).

Okamoto, et. al., Transgenic mice with increased expression of vascular endotheilal growth factor in the retina: a new model of intraretinal and subretinal neovascularization, Am. J. Pathol. 151:281-291 (1997).
Saishin, et al., "VEGF-TRAP(R1R2) suppresses choroidal neovascularization and VEGF-induced breakdown of the blood-retinal barrier", J. Cell Physiol., 195:241-8 (2003).
Singh, et al., "Cationic microparticles: A potent delivery system for DNA vaccines", PNAS, 98(2):811-6 (2000).
Smith, et al., Oxygen-induced retinopathy in the mouse, Invest. Ophthalmol. Vis. Sci. 35:101-111 (1994).
Sobczak, et al., "Synthesis and characterization of polyester conjugates of ciprofloxacin", Eu. J. Med Chem., 45(9):3844-9 (2010).
Soppimath, et al., "Biodegradable polymeric nanoparticles as drug delivery devise", J Cont. Release, 70:1-20 (2001).
Suh, et al., "PEGylation nanoparticles improves their cytoplasmic transport", Int. J Nanomed., 2(4):735-41 (2007).
Tanaka, et al., "Development of cell-penetrating peptide-modified MPEG-PCL diblock copolymeric nanoparticles for systemic gene delivery", Intl J Pharmac., 396(1-2):229-38 (2010).
Tang, et al., "Enhanced efficacy of local etoposide delivery by poly(ether-anhydride)particles against small cell lung cancer in vivo", Biomaterials, 31:339-44 (2010).
Tobe, et al., "Targeted disruption of the FGF2 gene does not prevent choroidal neovascularization in a murine model", Am. J. Pathol. 153:1641-1646 (1998).
Veronese, et al., "PEG-doxorubicin conjugates: influence of polymer structure on drug release, in vitro cytotoxicity, biodistribution, and antitumor activity", Bioconjig Chem., 16(4):775-84 (2005).
Yokoyama, et al., "Characterization and anticancer activity of the micelle-forming polymeric anticancer drug adriemycin-conjugated poly(ethylene glycol)-poly(aspartic acid) block copolymer", Cancer Res., 50:1693-1700 (1990).
Cynkowska, et al., "Novel antiglaucoma prodrugs and codrugs of ethacrynic acid", Bioorganic Med Chem. Ltrs., 15:3524-7 (2005).
Ghassabian, et al., "Role of human CYP3A4 in biotransformation of sorafenib to its major oxidized metabolites", Biochem Pharma., 84:215-23 (2012).
Koster, et al., "Single-molecule observations of topotecan-medicated TopIB activity at a unique DNA sequence", Nucleic Acids Res., 36(7):2301-10 (2008).
Na, et al., "Menadione and ethacrynic acid inhibit the hypoxia-inducible factor (HIF) pathway by disrupting HIF-1α interaction with p300", Biochem Biophysol Res Comm., 434:879-84 (2013).
Onnis, et al., "Development of HIF-1 inhibitors for cancer therapy", J Cell Mol Med., 13(9A):2780-6(2009).
Petersen, et al., "High-throughput analysis of protein stability in polyanhydride nanoparticles", Acta Biomat., 6:3873-81 (2010).
Xia, et al., "Recent advances inhypoxia-inducible factor (HIF)-1 inhibitors", Eu J Med Chem., 49:24-40 (2012) Abstract Only.

* cited by examiner

CONTROLLED RELEASE FORMULATIONS FOR THE DELIVERY OF HIF-1 INHIBITORS

CROSS REFERENCE TO RELATED APPLICATION

This application is a continuation application of pending prior application U.S. Ser. No. 13/797,506 filed Mar. 12, 2013, entitled "CONTROLLED RELEASE FORMULATIONS FOR THE DELIVERY OF HIF-1 INHIBITORS", by Justin Scot Hanes, Peter Anthony Campochiaro and Jie Fu, which claims benefit of U.S. Provisional Application No. 61/611,921 filed Mar. 16, 2012, all of which is herein incorporated by reference in their entirety.

SPONSORED RESEARCH OR DEVELOPMENT

This invention was made with Government Support under Agreements R01CA140746, P30EY001765, and U54CA151838 awarded to Justin Scot Hanes by the National Institutes of Health, and under Agreement R01EY012609 awarded to Peter Anthony Campochiaro by the National Institutes of Health. The Government has certain rights in the invention.

FIELD OF THE INVENTION

The present invention relates to polymeric controlled release formulations for the delivery of an effective amount of one or more HIF-1 inhibitors, in particular, to the eye, as well as methods of use thereof for the treatment and prevention of diseases, particularly for the treatment or prevention of ocular diseases.

BACKGROUND OF THE INVENTION

Hypoxia Inducible Factor 1 (HIF-1) is a transcription factor that controls expression of more than 60 target genes whose products are critical to many processes, including angiogenesis. For example, vascular endothelial growth factor (VEGF), the most important known regulator of angiogenesis, is upregulated by HIF-1. Active HIF-1 is composed of alpha (HIF-1α, 2α) and beta (HIF-1β) subunits that dimerize and bind to consensus sequences (hypoxia responsive elements, HREs) in the regulatory regions of the target genes. In normoxia, HIF-1 is hydroxylated and interacts with the von Hippel Lindau protein (pVHL), an E3 ubiquitin ligase subunit that targets HIF for degradation. In the absence of oxygen, HIF hydroxylation is inhibited, preventing binding to pVHL and leading to its intracellular accumulation. Increased levels of intracellular HIF-1α and HIF-2α have been associated with many aberrant vascularization processes.

Because of its critical role in angiogenesis, HIF-1 represents a promising target for the treatment and prevention of diseases and disorders associated with ocular neovascularization. Attempts to develop clinically useful therapies have been plagued by difficulty in administering and maintaining a therapeutically effective amount of HIF-1 inhibitors for an extended period of time. In addition, many HIF-1 inhibitors are cytotoxic, and exhibit significant side effects and/or toxicity, especially when administered to the ocular tissue.

In order to treat chronic diseases of the eye, there is a need for long acting methods for delivering HIF-1 inhibitors to the eye. Formulations which provide extended delivery of HIF-1 will minimize the potential for toxicity associated with the administration of many HIF-1 inhibitors. Formulations which provide extended delivery of HIF-1 will also sustain suppression of VEGF and other stimulators of angiogenesis, maximize efficacy, promote regression of neovascularization, and minimize the potential for catastrophic complications including subretinal hemorrhage. In addition, reducing the need for frequent injections will decrease the risk of endophthalmitis and decrease the burden of frequent clinic visits, a major hardship for patients and their families.

Therefore, it is an object of the invention to provide formulations of HIF-1 inhibitors with improved stability, safety, and efficacy.

It is also an object of the invention to provide drug formulations capable of effectively delivering therapeutic levels of one or more HIF-1 inhibitors for an extended period of time.

It is a further object of the invention to provide improved methods of treating or preventing diseases or disorders of the eye.

SUMMARY OF THE INVENTION

Controlled release dosage formulations for the delivery of one or more HIF-1 inhibitors conjugated to or dispersed in a polymeric vehicle for controlled delivery are described herein. The polymeric matrix can be formed from non-biodegradable or biodegradable polymers; however, the polymer matrix is preferably biodegradable. The polymeric matrix can be formed into implants (e.g., rods, disks, wafers, etc.), microparticles, nanoparticles, or combinations thereof for delivery. Upon administration, the one or more HIF-1 inhibitors are released over an extended period of time, either upon degradation of the polymer matrix, diffusion of the one or more inhibitors out of the polymer matrix, or a combination thereof. By employing a polymer-drug conjugate, particles can be formed with more controlled drug loading and drug release profiles. In addition, the solubility of the conjugate can be controlled so as to minimize soluble drug concentration and, therefore, toxicity.

In preferred embodiments, the one or more HIF-1 inhibitors are covalently bound to a polymer, forming a polymer-drug conjugate. The polymer-drug conjugates can then be formed into implants (e.g., rods, wafers, discs, etc), microparticles, nanoparticles, or combinations thereof for delivery to the eye. By employing a polymer-drug conjugate, particles can be formed with more controlled drug loading and drug release profiles. In addition, the solubility of the conjugate can be controlled by modifying the solubility of the polymer portion and/or the branched point ("Y" in the chemical structure of the polymer, so as to minimize soluble drug concentration and, therefore, toxicity.

In certain embodiments, the polymer-drug conjugates are block copolymers containing one or more HIF-1 inhibitors covalently bonded to the block copolymer. In one embodiment, the conjugate has the formula:

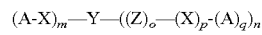

wherein

A represents, independently for each occurrence, a HIF-1 inhibitor;

X represents, independently for each occurrence, a hydrophobic polymer segment;

Y is absent or represents a branch point;

Z represents, independently for each occurrence, a hydrophilic polymer segment;

o, p, and q are independent 0 or 1;

m represents the number of A-X branches and is an integer between one and twenty; and n represent the number of Z, Z—X, and Z—X-A branches and is an integer between zero and twenty, more preferably between one and twenty, with the proviso that A is not doxorubicin when m and n are both equal to one.

Exemplary polymer-drug conjugates of this type are represented by the general formulae shown below

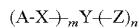

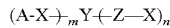

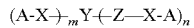

wherein

A represents, independently for each occurrence, a HIF-1 inhibitor;

X represents, independently for each occurrence, a hydrophobic polymer segment;

Y is absent or represents a branch point;

Z represents, independently for each occurrence, a hydrophilic polymer segment;

m represents the number of A-X branches and is an integer between one and twenty; and n represent the number of Z, Z—X, and Z—X-A branches and is an integer between zero and twenty, more preferably between one and twenty, with the proviso that A is not doxorubicin when m and n are both equal to one.

A is, independently for each occurrence, a HIF-1 inhibitor. In some instances, the HIF-1 inhibitor is an anthracycline, such as doxorubicin (DXR) or daunorubicin (DNR).

The one or more hydrophobic polymer segments can be any biocompatible, hydrophobic polymer or copolymer. In some cases, the hydrophobic polymer or copolymer is biodegradable. Examples of suitable hydrophobic polymers include, but are not limited to, polyesters such as polylactic acid, polyglycolic acid, or polycaprolactone, polyanhydrides, such as polysebacic anhydride, and copolymers of any of the above. In preferred embodiments, the hydrophobic polymer is a polyanhydride, such as polysebacic anhydride or a copolymer thereof.

The degradation profile of the one or more hydrophobic polymer segments may be selected to influence the release rate of the active agent in vivo. For example, the hydrophobic polymer segments can be selected to degrade over a time period from seven days to 2 years, more preferably from seven days to 56 weeks, more preferably from four weeks to 56 weeks, most preferably from eight weeks to 28 weeks.

The one or more hydrophilic polymer segments can be any hydrophilic, biocompatible, non-toxic polymer or copolymer. In certain embodiments, the one or more hydrophilic polymer segments contain a poly(alkylene glycol), such as polyethylene glycol (PEG). In particular embodiments, the one or more hydrophilic polymer segments are linear PEG chains.

In some embodiments, where both hydrophobic and hydrophilic polymer segments are present, the combined weight average molecular weight of the one or more hydrophilic polymer segments will preferably be larger than the weight average molecular weight of the hydrophobic polymer segment. In some cases, the combined weight average molecular weight of the hydrophilic polymer segments is at least five times, more preferably at least ten times, most preferably at least fifteen times, greater than the weight average molecular weight of the hydrophobic polymer segment.

The branch point, when present, can be an organic molecule which contains three or more functional groups. Preferably, the branch point will contain at least two different types of functional groups (e.g., one or more alcohols and one or more carboxylic acids, or one or more halides and one or more carboxylic acids). In such cases, the different functional groups present on the branch point can be independently addressed synthetically, permitting the covalent attachment of the hydrophobic and hydrophilic segments to the branch point in controlled stoichiometric ratios. In certain embodiments, the branch point is polycarboxylic acid, such as citric acid, tartaric acid, mucic acid, gluconic acid, or 5-hydroxybenzene-1,2,3,-tricarboxylic acid.

In certain embodiments, the polymer-drug conjugate is formed from a single hydrophobic polymer segment and two or more hydrophilic polymer segments covalently connected via a multivalent branch point. Exemplary polymer-drug conjugates of this type are represented by the general formula shown below

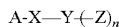

wherein

A represents a HIF-1 inhibitor;

X represents a hydrophobic polymer segment;

Y represents a branch point;

Z represents, independently for each occurrence, a hydrophilic polymer segment; and n is an integer between two and ten.

A is, independently for each occurrence, a HIF-1 inhibitor. In some instances, the HIF-1 inhibitor is an anthracycline, such as doxorubicin (DXR) or daunorubicin (DNR).

In certain embodiments, the hydrophilic polymer segments contain a poly(alkylene glycol), such as polyethylene glycol (PEG), preferably linear PEG chains. In some embodiments, the conjugates contain between two and six hydrophilic polymer segments.

In preferred embodiments, the hydrophobic polymer is a polyanhydride, such as polysebacic anhydride or a copolymer thereof. In certain embodiments, the hydrophobic polymer segment is poly(1,6-bis(p-carboxyphenoxy)hexane-co-sebacic acid) (poly(CPH-SA) or poly(1,3-bis(p-carboxyphenoxy)propane-co-sebacic acid) (poly(CPP-SA).

In some embodiments, the branch point connects a single hydrophobic polymer segment to three hydrophilic polyethylene glycol polymer segments. In certain cases, the polymer-drug conjugate can be represented by Formula I

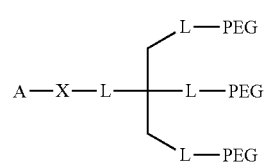

Formula I wherein

A is a HIF-1 inhibitor;

L represents, independently for each occurrence, an ether (e.g., —O—), thioether (e.g., —S—), secondary amine (e.g., —NH—), tertiary amine (e.g., —NR—), secondary amide (e.g., —NHCO—; —CONH—), tertiary amide (e.g., —NRCO—; —CONR—), secondary carbamate (e.g., —OCONH—; —NHCOO—), tertiary carbamate (e.g., —OCONR—; —NRCOO—), urea (e.g., —NHCONH—; —NRCONH—; —NHCONR—_, —NRCONR—), sulfinyl group (e.g., —SO—), or sulfonyl group (e.g., —SOO—);

R is, individually for each occurrence, an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;

PEG represents a polyethylene glycol chain; and

X represents a hydrophobic polymer segment.

In certain embodiments, the branch point is a citric acid molecule, and the hydrophilic polymer segments are polyethylene glycol. In such cases, the polymer-drug conjugate can be represented by Formula IA

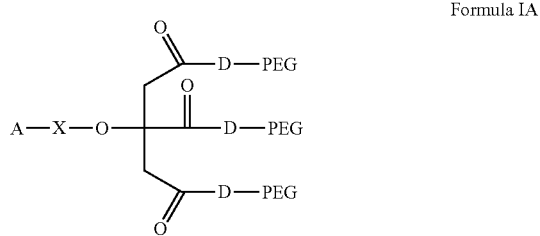

Formula IA wherein

A is a HIF-1 inhibitor;

D represents, independently for each occurrence, O or NH;

PEG represents a polyethylene glycol chain; and

X is represents a hydrophobic polymer segment.

X may be any biocompatible hydrophobic polymer or copolymer. In preferred embodiments, the hydrophobic polymer or copolymer is biodegradable. In preferred embodiments, the hydrophobic polymer is a polyanhydride, such as polysebacic anhydride, or a copolymer thereof.

The polymer-drug conjugates can be used to form implants (e.g., rods, discs, wafers, etc.), nanoparticles, or microparticles with improved properties for controlled delivery of HIF-1 inhibitors.

Also provided are pharmaceutical compositions containing implants (e.g., rods, discs, wafers, etc.), nanoparticles, microparticles, or combinations thereof for the controlled release of one or more HIF-1 inhibitors in combination with one or more pharmaceutically acceptable excipients. The nanoparticles, microparticles, or combination thereof can be formed from one or more polymer-drug conjugates, or blends of polymer-drug conjugates with one or more polymers. The implants (e.g., rods, discs, wafers, etc.), nanoparticles, microparticles, or combination thereof can also be formed from a polymeric matrix having one or more HIF-1 inhibitors dispersed or encapsulated therein.

The pharmaceutical compositions can be administered to treat or prevent a disease or disorder in a patient associated with vascularization, including cancer and obesity. In a preferred embodiment, the pharmaceutical compositions are administered to treat or prevent a disease or disorder in a patient associated with ocular neovascularization. Upon administration, the one or more HIF-1 inhibitors are released over an extended period of time at concentrations which are high enough to produce therapeutic benefit, but low enough to avoid unacceptable levels of cytotoxicity, and which provide much longer release than inhibitor without conjugate.

This is demonstrated in the case of controlled release formulations containing anthracyclines. The intravitreal injection of anthracyclines suppresses intraocular neovascularization; however, the effect is short-lived because the anthracyclines are rapidly eliminated from the posterior segment of the eye. In addition, the anthracyclines are too toxic for clinical use, as indicated by a severe reduction in scoptopic ERG b-wave amplitudes and retinal degeneration. However, administration of a controlled release formulation of an anthracycline (e.g., nanoparticles formed from a polymer-drug conjugate defined by Formula I) provides enhanced and prolonged anti-angiogenic activity with no signs of toxicity. The controlled release HIF-1 formulation provides prolonged therapeutic benefit in the absence of side effects by releasing low levels of an HIF-1 inhibitor over a prolonged period of time.

BRIEF DESCRIPTION OF THE DRAWINGS

FIG. 1A plots the area of CNV (in $mm^2$) observed in the eyes of C57BL/6 mice 14 days after rupture of their Bruch's membrane by laser photocoagulation without administration of a HIF-1 inhibitor (vehicle only injected in both eyes of the mouse (BE), left bar), and upon administration of 10, 1.0, and 0.1 μg of daunorubicin (DNR). Eyes injected with 10 μg of DNR showed a statistically significant reduction in the area of CNV ($P<0.001$, n=10) compared to fellow eyes injected with the vehicle only. Eyes injected with 1.0 μg and 0.1 μg of DNR did not show a statistically significant reduction in the area of CNV (for 1.0 μg, $P<0.082$, n=10; for 0.1 μg, $P<0.399$, n=10) compared to fellow eyes injected with the vehicle only. FIG. 1B plots the area of CNV (in $mm^2$) observed in the eyes of C57BL/6 mice 14 days after rupture of their Bruch's membrane by laser photocoagulation without administration of a HIF-1 inhibitor (vehicle only injected in both eyes of the mouse (BE), left bar), and upon administration of 10, 1.0, and 0.1 μg of doxorubicin (DXR, open bars). Eyes injected with 10 μg of DXR showed a statistically significant reduction in the area of CNV ($P<0.001$, n=10) compared to fellow eyes injected with the vehicle only. Eyes injected with 1.0 μg and 0.1 μg of DXR did not show a statistically significant reduction in the area of CNV (for 1.0 μg, $P<0.071$, n=10; for 0.1 μg, $P<0.322$, n=10) compared to fellow eyes injected with the vehicle only. In both FIGS. 1A and 1B, the mean area of CNV was similar in fellow eyes (FE) and eyes from mice in which both eyes were injected with vehicle only (BE), suggesting that there was no systemic effect from intraocular injections of the HIF-1 inhibitor.

FIG. 2A plots the area of RNV (in $mm^2$) observed in the eyes of C57BL/6 mice with oxygen-induced ischemic retinopathy five days after the administration of a vehicle control (PBS buffer without a HIF-1 inhibitor present, left bar), and upon administration of 1.0, 0.1, and 0.01 μg of daunorubicin (DNR). Eyes injected with 1.0 μg and 0.1 μg of DNR showed a statistically significant reduction in the area of RNV (for 1 µg, P<0.001, n=6; for 0.1 µg, P=0.013, n=8). Eyes injected with 0.01 µg of DNR did not show a statistically significant reduction in the area of RNV (P=0.930, n=6). FIG. 2B plots the area of RNV (in mm$^2$) observed in the eyes of C57BL/6 mice with oxygen-induced ischemic retinopathy five days after the administration of a vehicle control (PBS buffer without a HIF-1 inhibitor present, left bar), and upon administration of 1.0, 0.1, and 0.01 µg of doxorubicin (DXR). Eyes injected with 1.0 µg of DXR showed a statistically significant reduction in the area of RNV (P<0.001, n=8). Eyes injected with 0.1 µg and 0.01 µg of DXR did not show a statistically significant reduction in the area of RNV (for 0.1 µg, P=0.199, n=7; for 0.01 µg, P=0.096, n=8).

FIG. 3A is a bar graph plotting the area of CNV (in mm$^2$) observed in the eyes of C57BL/6 mice 14 days after rupture of their Bruch's membrane by laser photocoagulation without administration of a HIF-1 inhibitor (vehicle only injected in both eyes of the mouse (BE), left bar), and upon administration of 10, 1.0, and 0.1 µg of DXR-PSA-PEG$_3$ nanoparticles. In the case of values of CNV measured upon administration of varying amounts of DXR-PSA-PEG$_3$ nanoparticles, the area of CNV observed upon nanoparticle administration is plotted next to the area of CNV observed in untreated fellow eyes (FE). The bars represent the mean (±SEM) area of CNV. Eyes injected with 10 µg, 1.0 µg, and 0.1 µg of DXR-PSA-PEG$_3$ nanoparticles all showed a statistically significant reduction in the area of CNV (for 10 µg, P<0.001, n=10; for 1.0 µg, P=0.009, n=10; for 0.1 µg, P=0.007, n=10) compared to fellow eyes injected with the vehicle only.

FIG. 3B is a bar graph plotting the area of CNV (in mm$^2$) observed seven days after administration of 1 µg of DXR-PSA-PEG$_3$ nanoparticles (left bar) and 14 days after laser photocoagulation rupture of Bruch's membrane. The area of CNV (in mm$^2$) observed seven days after administration of 1 µg of DXR-PSA-PEG$_3$ nanoparticles and 14 days after laser photocoagulation rupture of Bruch's membrane is compared with the area of CNV measured in fellow eyes injected with vehicle only (center bar) 14 days after laser photocoagulation rupture of Bruch's membrane and seven days after vehicle injection and untreated eyes seven days after laser photocoagulation rupture of Bruch's membrane (Base line; right bar). A statistically significant decrease in the area of CNV (P<0.001, n=10) was observed, both relative to fellow eyes injected with vehicle only (center bar) and the base line CNV observed seven days after laser photocoagulation rupture of Bruch's membrane in untreated eyes (right bar), demonstrating that DXR-PSA-PEG$_3$ treatment not only significantly reduced CNV (compare left and middle bars), but also mediated regression of existing CNV (compare left and right bars).

FIG. 4 is a bar graph plotting the area of RNV (in mm$^2$) observed in the eyes of C57BL/6 mice with oxygen-induced ischemic retinopathy five days after the administration of a vehicle control (PBS buffer without a HIF-1 inhibitor present, right bar), and upon administration of 1 µg of DXR-PSA-PEG$_3$ nanoparticles (left bar). The bars represent the mean (±SEM) area of RNV. A statistically significant decrease in the area of RNV (P<0.001, n=8) was observed relative to fellow eyes injected with vehicle only.

FIG. 5A is a bar graph plotting the area of NV (in mm$^2$) per retina observed four weeks after intraocular injection of 10 µg of DXR-PSA-PEG$_3$ nanoparticles (left bar). A statistically significant decrease in the area of NV per retina (P=0.042, n=5) was observed relative to fellow eyes injected with vehicle only. FIG. 5B is a bar graph plotting the area of NV (in mm$^2$) per retina observed five weeks after intraocular injection of 10 µg of DXR-PSA-PEG$_3$ nanoparticles (left bar). A statistically significant decrease in the area of NV per retina (P=0.007, n=5) was observed relative to fellow eyes injected with vehicle only.

DETAILED DESCRIPTION OF THE INVENTION

I. Definitions

Figure 1A:
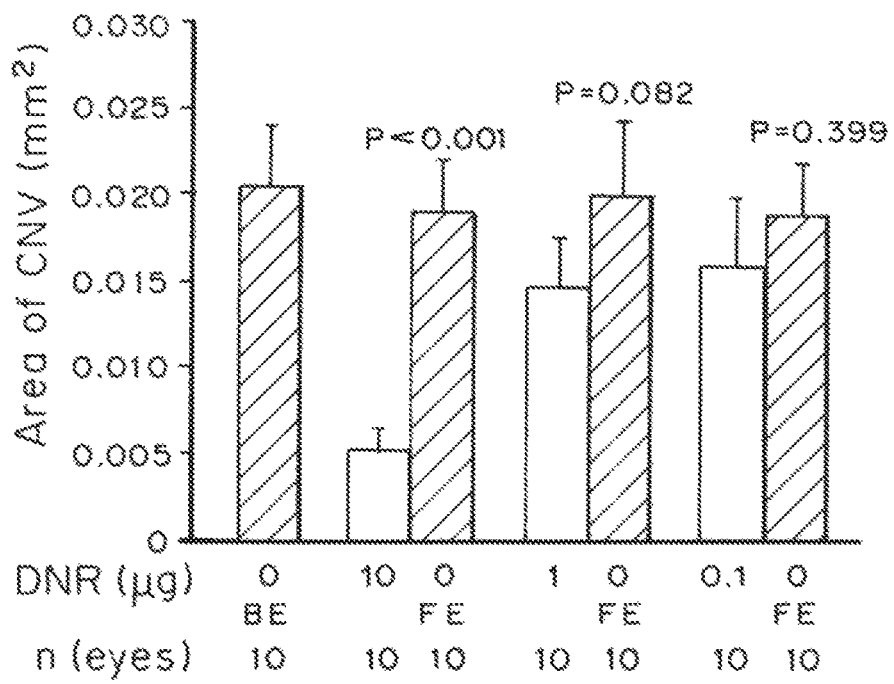
FIGS. 1A-B are bar graphs plotting the area of choroidal neovascularization (CNV) (in $mm^2$) observed in the eyes of C57BL/6 mice 14 days after rupture of their Bruch's membrane by laser photocoagulation without administration of a HIF-1 inhibitor, and upon administration of varying amounts of doxorubicin or daunorubicin. In the case of values of CNV measured upon HIF-1 administration, the area of CNV observed upon HIF-1 administration (open bars) is plotted next to the area of CNV observed in untreated fellow eyes (FE). The bars represent the mean (±SEM) area of choroidal NV.

"Active Agent," as used herein, refers to a physiologically or pharmacologically active substance that acts locally and/ or systemically in the body. An active agent is a substance that is administered to a patient for the treatment (e.g., therapeutic agent), prevention (e.g., prophylactic agent), or diagnosis (e.g., diagnostic agent) of a disease or disorder. "Ophthalmic Drug" or "Ophthalmic Active Agent", as used herein, refers to an agent that is administered to a patient to alleviate, delay onset of, or prevent one or more symptoms of a disease or disorder of the eye, or diagnostic agent useful for imaging or otherwise assessing the eye.

"Effective amount" or "therapeutically effective amount," as used herein, refers to an amount of polymer-drug conjugate effective to alleviate, delay onset of, or prevent one or more symptoms, particularly of a disease or disorder of the eye. In the case of age-related macular degeneration, the effective amount of the polymer-drug conjugate delays, reduces, or prevents vision loss in a patient.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as but not limited to a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

"Nanoparticle," as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle," as used herein, generally refers to a particle having a diameter, such as an average diameter, from about 1 micron to about 100 microns, preferably from about 1 micron to about 50 microns, more preferably from about 1 to about 30 microns. The microparticles can have any shape. Microparticles having a spherical shape are generally referred to as "microspheres".

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution" are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Pharmaceutically Acceptable," as used herein, refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Branch point," as used herein, refers to a portion of a polymer-drug conjugate that serves to connect multiple hydrophilic polymer segments to one end of the hydrophobic polymer segment or multiple hydrophobic polymer segments to one end of the hydrophilic segment.

"HIF-1 inhibitor," as used herein, refers to, a drug that reduces the level of HIF-1 and/or its ability to stimulate the transcription of genes that contain a hypoxia response element in their promoter region.

"Implant," as generally used herein, refers to a polymeric device or element that is structured, sized, or otherwise configured to be implanted, preferably by injection or surgical implantation, in a specific region of the body so as to provide therapeutic benefit by releasing one or more HIF-1 inhibitors over an extended period of time at the site of implantation. For example, intraocular implants are polymeric devices or elements that are structured, sized, or otherwise configured to be placed in the eye, preferably by injection or surgical implantation, and to treat one or more diseases or disorders of the eye by releasing one or more HIF-1 inhibitors over an extended period. Intraocular implants are generally biocompatible with physiological conditions of an eye and do not cause adverse side effects. Generally, intraocular implants may be placed in an eye without disrupting vision of the eye.

Ranges of values defined herein include all values within the range as well as all sub-ranges within the range. For example, if the range is defined as an integer from 0 to 10, the range encompasses all integers within the range and any and all subranges within the range, e.g., 1-10, 1-6, 2-8, 3-7, 3-9, etc.

II. Polymer-Drug Conjugates

Controlled release conjugates including one or more HIF-1 inhibitors conjugated to or dispersed in a polymeric vehicle for controlled release of the one or more HIF-1 inhibitors are provided. By administering controlled release conjugates of HIF-1 inhibitors, activity is enhanced and prolonged while toxicity is reduced or eliminated.

In some embodiments, one or more HIF-1 inhibitors are dispersed or encapsulated in a polymeric matrix for delivery to the eye. The polymeric matrix can be formed from non-biodegradable or biodegradable polymers; however, the polymer matrix is preferably biodegradable. The polymeric matrix can be formed into implants, microparticles, nanoparticles, or combinations thereof for delivery to the eye. Upon administration, the one or more HIF-1 inhibitors are released over an extended period of time, either upon degradation of the polymer matrix, diffusion of the one or more inhibitors out of the polymer matrix, or a combination thereof. By employing a polymer-drug conjugate, particles can be formed with more controlled drug loading and drug release profiles.

In some embodiments, the controlled-release formulation contains particles formed from one or more polymer-drug conjugates. The polymer-drug conjugates are block copolymers containing one or more HIF-1 inhibitors covalently bonded to the block copolymer. Typically, the polymer-drug conjugates contain a HIF-1 inhibitor, one or more hydrophobic polymer segments, and one or more hydrophilic polymer segments. In certain cases, one or more hydrophilic polymer segments are attached to the one or more hydrophobic polymer segments by a branch point. By employing a polymer-drug conjugate, particles can be formed with more controlled drug loading and drug release profiles. In addition, the solubility of the conjugate can be controlled so as to minimize soluble drug concentration and, therefore, toxicity.

In certain embodiments, the polymer-drug conjugate contains one or more HIF-1 inhibitors covalently attached to a bioerodible polymeric segment. Preferably, the bioerodible segment to which the HIF-1 inhibitor is attached is composed of one or more monomers that possess low solubility in aqueous solution. In certain embodiments, one or more of the monomers possesses a solubility of less than 2 g/L, more preferably less than 1 g/L, more preferably less than 0.5 g/L, most preferably less than 0.3 g/L in water.

A. Structure of the Polymer-Drug Conjugates

Polymer-drug conjugates are provided which contain a HIF-1 inhibitor covalently attached to a block copolymer.

In one embodiment, the conjugate has the formula:

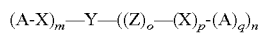

wherein

A represents, independently for each occurrence, a HIF-1 inhibitor;

X represents, independently for each occurrence, a hydrophobic polymer segment;

Y is absent or represents a branch point;

Z represents, independently for each occurrence, a hydrophilic polymer segment;

o, p, and q are independent 0 or 1;

m represents the number of A-X branches and is an integer between one and twenty; and n represent the number of Z, Z—X, and Z—X-A branches and is an integer between zero and twenty, more preferably between one and twenty, with the proviso that A is not doxorubicin when m and n are both equal to one.

Exemplary polymer-drug conjugates are represented by the general formulae shown below:

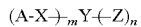

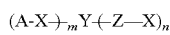

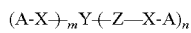

wherein

A represents, independently for each occurrence, a HIF-1 inhibitor;

X represents, independently for each occurrence, a hydrophobic polymer segment;

Y is absent, or represents a branch point;

Z represents, independently for each occurrence, a hydrophilic polymer segment; and m represents the number of A-X branches and is an integer between one and twenty; and n represents the number of Z, Z—X, and Z—X-A branches and is an integer between zero and twenty, more preferably between one and 20, with the proviso that A is not doxorubicin when m and n are both equal to one.

A is, independently for each occurrence, aHIF-1 inhibitor. In some instances, the active agent is an anthracycline, such as doxorubicin (DXR) or daunorubicin (DNR).

The one or more hydrophobic polymer segments can be any biocompatible, hydrophobic polymer or copolymer. In some cases, the hydrophobic polymer or copolymer is biodegradable. Examples of suitable hydrophobic polymers include, but are not limited to, polyesters such as polylactic acid, polyglycolic acid, or polycaprolactone, polyanhydrides, such as polysebacic anhydride, and copolymers thereof. In preferred embodiments, the hydrophobic polymer is a polyanhydride, such as polysebacic anhydride or a copolymer thereof.

The degradation profile of the one or more hydrophobic polymer segments may be selected to influence the release rate of the active agent in vivo. For example, the hydrophobic polymer segments can be selected to degrade over a time period from seven days to 2 years, more preferably from seven days to 56 weeks, more preferably from four weeks to 56 weeks, most preferably from eight weeks to 28 weeks.

The one or more hydrophilic polymer segments can be any hydrophilic, biocompatible, non-toxic polymer or copolymer. In certain embodiments, the one or more hydrophilic polymer segments contain a poly(alkylene glycol), such as polyethylene glycol (PEG). In particular embodiments, the one or more hydrophilic polymer segments are linear PEG chains.

In some cases, the polymer-drug conjugate contains only one hydrophilic polymer segment (i.e., n is equal to one). In preferred embodiments, the polymer-drug conjugate contains more than one hydrophilic polymer chain (i.e., n is greater than one). In certain embodiments, the polymer-drug conjugate contains between two and six, more preferably between three and five hydrophilic polymer chains. In one embodiment, the polymer drug conjugate contains three hydrophilic polymer segments.

In cases where both hydrophobic and hydrophilic polymer segments are present, the combined molecular weight of the one or more hydrophilic polymer segments will preferably be larger than the molecular weight of the hydrophobic polymer segment. In some cases, the combined molecular weight of the hydrophilic polymer segments is at least five times, more preferably at least ten times, most preferably at least fifteen times, greater than the molecular weight of the hydrophobic polymer segment.

The branch point, when present, can be an organic molecule which contains three or more functional groups. Preferably, the branch point will contain at least two different types of functional groups (e.g., one or more alcohols and one or more carboxylic acids, or one or more halides and one or more carboxylic acids or one or more amines)). In such cases, the different functional groups present on the branch point can be independently addressed synthetically, permitting the covalent attachment of the hydrophobic and hydrophilic segments to the branch point in controlled stoichiometric ratios. In certain embodiments, the branch point is polycarboxylic acid, such as citric acid, tartaric acid, mucic acid, gluconic acid, or 5-hydroxybenzene-1,2,3,-tricarboxylic acid.

In certain embodiments, the polymer-drug conjugate is formed from a single hydrophobic polymer segment and two or more hydrophilic polymer segments covalently connected via a multivalent branch point. Exemplary polymer-drug conjugates of this type are represented by the general formula shown below

wherein
A represents, independently for each occurrence, a HIF-1 inhibitor;
X represents, a hydrophobic polymer segment;
Y represents a branch point;
Z represents, independently for each occurrence, a hydrophilic polymer segment; and
n is an integer between zero and 300, more preferably between zero and fifty, more preferably between zero and thirty, most preferably between zero and ten.

A is, independently for each occurrence, a HIF-1 inhibitor. In some instances, the HIF-1 inhibitor is an anthracycline, such as doxorubicin (DXR) or daunorubicin (DNR).

The hydrophobic polymer segment can be any biocompatible hydrophobic polymer or copolymer. In some cases, the hydrophobic polymer segment is also biodegradable. Examples of suitable hydrophobic polymers include, but are not limited to, copolymers of lactic acid and glycolic acid, polyanhydrides, poylcaprolactone, and copolymers thereof. In certain embodiments, the hydrophobic polymer is a polyanhydride, such as polysebacic anhydride.

The one or more hydrophilic polymer segments can be any hydrophilic, biocompatible, non-toxic polymer or copolymer. The hydrophilic polymer segment can be, for example, a poly(alkylene glycol), a polysaccharide, poly(vinyl alcohol), polypyrrolidone, or copolymers thereof. In preferred embodiments, the one or more hydrophilic polymer segments are, or are composed of, polyethylene glycol (PEG).

In certain embodiments, the polymer-drug conjugate contains between two and six, more preferably between three and five, hydrophilic polymer chains. In one embodiment, the polymer drug conjugate contains three hydrophilic polymer segments.

The branch point can be, for example, an organic molecule which contains multiple functional groups. Preferably, the branch point will contain at least two different types of functional groups (e.g., an alcohol and multiple carboxylic acids, or a carboxylic acid and multiple alcohols). In certain embodiments, the branch point is polycarboxylic acid, such as a citric acid molecule.

In some embodiments, the branch point connects a single hydrophobic polymer segment to three hydrophilic polyethylene glycol polymer segments. In certain cases, the polymer-drug conjugate can be represented by Formula I

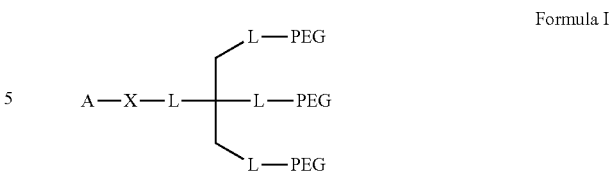

wherein
A is a HIF-1 inhibitor;
L represents, independently for each occurrence, an ether (e.g., —O—), thioether (e.g., —S—), secondary amine (e.g., —NH—), tertiary amine (e.g., —NR—), secondary amide (e.g., —NHCO—; —CONH—), tertiary amide (e.g., —NRCO—; —CONR—), secondary carbamate (e.g., —OCONH—; —NHCOO—), tertiary carbamate (e.g., —OCONR—; —NRCOO—), urea (e.g., —NHCONH—; —NRCONH—; —NHCONR—, —NRCONR—), sulfinyl group (e.g., —SO—), or sulfonyl group (e.g., —SOO—);
R is, individually for each occurrence, an alkyl, cycloalkyl, heterocycloalkyl, alkylaryl, alkenyl, alkynyl, aryl, or heteroaryl group, optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl;
PEG represents a polyethylene glycol chain; and
X represents a hydrophobic polymer segment.

In certain embodiments, the branch point is a citric acid molecule, and the hydrophilic polymer segments are polyethylene glycol. In such cases, the polymer-drug conjugate can be represented by Formula IA

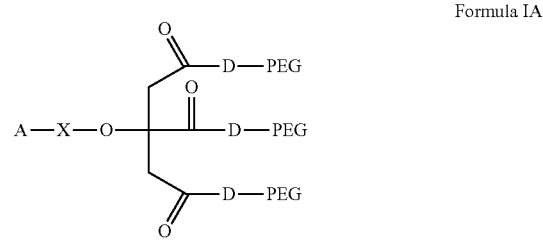

wherein
A is a HIF-1 inhibitor;
D represents, independently for each occurrence, O or NH;
PEG represents a polyethylene glycol chain; and
X is represents a hydrophobic polymer segment.

In some embodiments, D is, in every occurrence, O. In other embodiments, D is, in every occurrence, NH. In still other embodiments, D is, independently for each occurrence, O or NH.

In some embodiments, the polymer drug conjugate is defined by the following formula

A-X wherein
A is a HIF-1 inhibitor; and
X is a hydrophobic polymer segment, preferably a polyanhydride.

B. HIF-1 Inhibitors

The polymer-drug conjugates contain one or more HIF-1 inhibitors. Any suitable HIF-1 inhibitor may be incorporated into the polymer-drug conjugates. Preferably, the one or more HIF-1 inhibitors are HIF-1α inhibitors. The inhibitors can be small molecules and/or a biomolecule or macromolecule (e.g., proteins, enzymes, nucleic acids, growth factors, polysaccharides, lipids, etc.). In some instances, the small molecule active agent has a molecular weight of less than about 2000 g/mol, preferably less than about 1500 g/mol, more preferably less than about 1200 g/mol, most preferably less than about 1000 g/mol. In other embodiments, the small molecule active agent has a molecular weight less than about 500 g/mol. Biomolecules typically have a molecular weight of greater than about 2000 g/mol and may be composed of repeat units such as amino acids (peptide, proteins, enzymes, etc.) or nitrogenous base units (nucleic acids).

In a preferred embodiment, the one or more HIF-1 inhibitors are anthracyclines. Anthracyclines, such as doxorubicin (DXR) and daunorubicin (DNR), are cancer chemotherapeutic agents that bind to DNA and suppress proliferation of cancer cells. Independent of their activity on cell proliferation, DXR and DNR suppress transcriptional activity of HIF-1.

Anthracyclines are glycosides whose aglycone is a tetracyclic anthraquinone derivative. Encompassed within the term anthracycline are compounds of the anthracycline class of natural products, as well as synthetic or semi-synthetic analogs and derivatives thereof, prodrugs thereof, and pharmaceutically acceptable salts thereof. "Analogs" and "derivatives" as used herein typically refers to compounds which retain the anthracycline core, i.e., the tetracyclic core, but differ in one or more functional groups attached to the core. In some embodiments, the derivatives and analogs differ in the aglycone moiety and/or the sugar residue attached to the molecule.

Any anthracycline which provides therapeutic benefit may be incorporated into the polymer-drug conjugates. Preferably, the anthracycline is a compound which is used or suitable for clinical use as an antineoplastic agent in cancer chemotherapy. Examples of natural products in the anthracycline class include daunorubicin and doxorubicin, which are produced by microorganisms belonging to the genus *Streptomyces*.

Examples of preferred anthracyclines include doxorubicin, daunorubicin, 13-deoxydoxorubicin (also known as GPX-100), iodoxorubicin, epirubicin, THP-adriamycin, idarubicin, menogaril, aclacinomycin A (also known as aclarubicin), zorubicin, pirarubicin, valrubicin, amrubicin, iodoxorubicin, nemorubicin, (4R)-1-(4-carboxy-1-oxobutyl)-4-hydroxy-L-prolyl-L-alanyl-L-seryl(2R)-2-cyclohexylglycyl-L-glutaminyl-L-seryl-L-leucine (also known as L 377202), 4'deoxy-4'-iododoxorubicin. Additional anthracyclines that can be incorporated in polymer-drug conjugates are known in the art. See, for example, Suarato, et al. Chimicaoggi, 9-19 (April 1990); J W Lown: Pharmac. Ther. 60:185-214 (1993); F M Arcamone: Biochimie, 80, 201-206 (1998); C Monneret: Eur. J. Med. Chem. 36: 483-493 (2001); and U.S. Pat. Nos. 4,438,015, 4,672,057, 5,646,177, 5,801,257, and 6,284,737.

The polymer-drug conjugate can also contain a pharmaceutically acceptable salt of an anthracycline. In some cases, it may be desirable to incorporate a salt of an anthracycline into a polymer-drug conjugate due to one or more of the salt's advantageous physical properties, such as enhanced stability or a desirable solubility or dissolution profile. Salts of anthracycline compounds can be prepared using standard methods known in the art. Lists of suitable salts can be found, for example, in Remington's Pharmaceutical Sciences, 20th ed., Lippincott Williams & Wilkins, Baltimore, Md., 2000, p. 704.

The polymer-drug conjugate can also contain a prodrug of an anthracycline. Anthracycline prodrugs are compounds that can be converted to a biologically active anthracycline, either in vivo after administration or in vitro prior to administration of the compound. Examples of suitable anthracycline prodrugs are known in the art. See, for example, U.S. Pat. No. 5,710,135 Leenders, et al., U.S. Pat. No. 6,268,488 by Barbas, III, et al., WO 92/19639 by J. lacquesy et al., K. Bosslet et al. Cancer Res. 54: 2151-2159 (1994), S. Andrianomenjanahary et al. Bioorg. Med. Chem Lett. 2:1093-1096 (1992) and J.-P. Gesson et al. Anti-Cancer Drug Des. 9: 409-423 (1994).

Other suitable HIF-1 inhibitors include, without limitation, polyamides such as echinomycin (NSC-13502) (Kong, et al., Cancer Research. 65(19): 9047-9055 (2005) and Olenyuk et al, Proc Natl Acad Sci USA 101: 1676816773 (2004)), which inhibit the interaction between HIF and DNA; epidithiodiketopiperazines, such as chetomin (Kung, et al., Cancer Cell. 6(3): 33-43 (2004)), which inhibit the interaction between HIF and p300; benzoazaheterocycles, such as YC-1 (3-(5'-hydroxymethyl-2'-furyl)-1-benzylindazole) (Yeo, et al., Journal of the National Cancer Institute. 95(7): 516-525 (2003)); radicicol and analogs thereof such as KF58333 (Kurebayashi, et al., Cancer Research 92:1342-1351 (2001)); rapamycins, including rapamycin and analogs thereof such as, temsirolimus (CCI779) and Everolimus (RAD001) (Majumder et al. Nature Medicine 10: 594-601 (2004)); geldanamycins, including geldanamycin and analogs thereof such as 17-allylamino-17-demethoxy geldanamycin (17-AAG), and 17-dimethylaminoethylamino-17-demethoxy-geldanamycin (17-DMAG); quinocarmycin monocitrate (KW2152) and its hydrocyanization product DX-52-1 (NSC-607097) (Rapisarda, et al. Cancer Research. 62(15): 43164324 (2002)); camptothecin analogs (topoisomerase I inhibitors) (Rapisarda, et al., Cancer Research 62(15): 4316-4324 (2002)), such as topotecan (NSC609699), camptothecin, 20-ester(S) (NSC-606985), and. 9-glycineamido-20(S)-camptothecin HCl (NSC-639174); microtubule disrupting agents (Escuin, et al. Cancer Research 65(19): 9021-9028 (2005)), such as paclitaxel, docetaxel, 2-methoxyestradiol, vincristine, discodermolide, and epothilone B; thioredoxin inhibitors (Welsh, et al. Molecular Cancer Therapeutics. 2:235243 (2003)), such as PX-12 (1-methylpropyl 2-imidazolyl disulfide) and Pleurotin; P13-Kinase Inhibitors (Jiang, et al. Cell Growth and Differentiation 12: 363-369 (2001)), such as wortmannin and LY294002; protein kinase-1 (MEK-1) inhibitors such as PD98059 (2'-amino-3'methoxyflavone); PX-12 (1-methylpropyl 2-imidazolyl disulfide); pleurotin PX-478; quinoxaline 1,4-dioxides; sodium butyrate (NaB); sodium nitropurruside (SNP); 103D5R (Tan, et al., Cancer Research 65: 605-612 (2005)); PX-478 (S-2-amino3-[4V—N,N,-bis(2-chloroethyl)amino]-phenyl propionic acid N-oxide dihydrochloride) (Welsh, et al., Molecular Cancer Therapeutics 3: 233-244 (2004)); histone deacetylase inhibitors such as [(E)-(1S,4S,10S,21R)-7-[(Z)-ethylidene]-4,21-diisopropyl-2-oxa-12, 13-dithia-5,8,20,23-tetraazabicyclo-[8,7,6]-tricos-16-ene-3,6,9,19,22-pentanone (FR901228, depsipeptide) and FK228 (FR901228) (NSC 630176) (Mie-Lee, et al., Biochemical and Biophysical Research Communications 300(1): 241-246 (2003)); genistein; indanone; staurosporin; coumarins; barbituric and thiobarbituric acid analogs; (aryloxyacetylamino)benzoic acid analogs, 2-methoxyestradiol and analogs thereof, digoxin and other cardiac glycosides (Zhang, et al. PNAS 105:19579), acriflavin (Lee, et al. PNAS 106:17910), and hydroxamic acid compounds.

In certain embodiments, the HIF-1 inhibitor is rapamycin, temsirolimus, everolimus, geldanamycin, echinomycin, doxorubicin, daunorubicin, camptothecin, topotecan, irinotecan, or bortezomib.

C. Hydrophobic Polymer Segment

Polymer-drug conjugates can contain one or more hydrophobic polymer segments. The hydrophobic polymer segments can be homopolymers or copolymers.

In preferred embodiments, the hydrophobic polymer segment is a biodegradable polymer. In cases where the hydrophobic polymer is biodegradable, the polymer degradation profile may be selected to influence the release rate of the active agent in vivo. For example, the hydrophobic polymer segment can be selected to degrade over a time period from seven days to 2 years, more preferably from seven days to 56 weeks, more preferably from four weeks to 56 weeks, most preferably from eight weeks to 28 weeks.

Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(hydroxyalkanoates); poly (lactide-co-caprolactones); polycarbonates such as tyrosine polycarbonates; polyamides (including synthetic and natural polyamides), polypeptides, and poly(amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In preferred embodiments, the hydrophobic polymer segment is a polyanhydride. The polyanhydride can be an aliphatic polyanhydride, an unsaturated polyanhydride, or an aromatic polyanhydride. Representative polyanhydrides include polyadipic anhydride, polyfumaric anhydride, polysebacic anhydride, polymaleic anhydride, polymalic anhydride, polyphthalic anhydride, polyisophthalic anhydride, polyaspartic anhydride, polyterephthalic anhydride, polyisophthalic anhydride, poly carboxyphenoxypropane anhydride, polycarboxyphenoxyhexane anhydride, as well as copolymers of these polyanhydrides with other polyanhydrides at different mole ratios. Other suitable polyanhydrides are disclosed in U.S. Pat. Nos. 4,757,128, 4,857,311, 4,888, 176, and 4,789,724. The polyanhydride can also be a copolymer containing polyanhydride blocks.

In certain embodiments, the hydrophobic polymer segment is polysebacic anhydride. In certain embodiments, the hydrophobic polymer segment is poly(1,6-bis(p-carboxyphenoxy)hexane-co-sebacic acid) (poly(CPH-SA). In certain embodiments, the hydrophobic polymer segment is poly(1,3-bis(p-carboxyphenoxy)propane-co-sebacic acid) (poly(CPP-SA).

The molecular weight of the hydrophobic polymer can be varied to prepare polymer-drug conjugates that form particles having properties, such as drug release rate, optimal for specific applications. The hydrophobic polymer segment can have a molecular weight of about 150 Da to 1 MDa. In certain embodiments, the hydrophobic polymer segment has a molecular weight of between about 1 kDa and about 100 kDa, more preferably between about 1 kDa and about 50 kDa, most preferably between about 1 kDa and about 25 kDa.

In some cases, the hydrophobic polymer segment has a molecular weight which is less that the average molecular weight of the one or more hydrophilic polymer segments of the polymer-drug conjugate. In a preferred embodiment, the hydrophobic polymer segment has a molecular weight of less than about 5 kDa.

D. Hydrophilic Polymers

Polymer-drug conjugates can also contain one or more hydrophilic polymer segments. Preferably, the polymer-drug conjugates contain more than one hydrophilic polymer segment. In some embodiments, the polymer-drug conjugate contains between two and six, more preferably between three and five, hydrophilic polymer segments. In certain embodiments, the polymer drug conjugate contains three hydrophilic polymer segments.

Each hydrophilic polymer segment can independently be any hydrophilic, biocompatible (i.e., it does not induce a significant inflammatory or immune response), non-toxic polymer or copolymer. Examples of suitable polymers include, but are not limited to, poly(alkylene glycols) such as polyethylene glycol (PEG), poly(propylene glycol) (PPG), and copolymers of ethylene glycol and propylene glycol, poly(oxyethylated polyol), poly(olefinic alcohol), polyvinylpyrrolidone), poly(hydroxyalkylmethacrylamide), poly(hydroxyalkylmethacrylate), poly(saccharides), poly (amino acids), poly(hydroxy acids), poly(vinyl alcohol), and copolymers, terpolymers, and mixtures thereof.

In preferred embodiments, the one or more hydrophilic polymer segments contain a poly(alkylene glycol) chain. The poly(alkylene glycol) chains may contain between 8 and 500 repeat units, more preferably between 40 and 500 repeat units. Suitable poly(alkylene glycols) include polyethylene glycol), polypropylene 1,2-glycol, poly(propylene oxide), polypropylene 1,3-glycol, and copolymers thereof. In certain embodiments, the one or more hydrophilic polymer segments are PEG chains. In such cases, the PEG chains can be linear or branched, such as those described in U.S. Pat. No. 5,932,462. In certain embodiments, the PEG chains are linear.

Each of the one or more hydrophilic polymer segments can independently have a molecular weight of about 300 Da to 1 MDa. The hydrophilic polymer segment may have a molecular weight ranging between any of the molecular weights listed above. In certain embodiments, each of the one or more hydrophilic polymer segments has a molecular weight of between about 1 kDa and about 20 kDa, more preferably between about 1 kDa and about 15 kDa, most preferably between about 1 kDa and about 10 kDa. In a preferred embodiment, each of the one or more hydrophilic polymer segments has a molecular weight of about 5 kDa.

E. Branch Points

The conjugates optionally contain a branch point which serves to connect multiple hydrophilic polymer segments to one end of the hydrophobic polymer segment. The branch point can be any organic, inorganic, or organometallic moiety which is polyvalent, so as to provide more than two points of attachment. In preferred embodiments, the branch point is an organic molecule which contains multiple functional groups.

The functional groups may be any atom or group of atoms that contains at least one atom that is neither carbon nor hydrogen, with the proviso that the groups must be capable of reacting with the hydrophobic and hydrophilic polymer segments. Suitable functional groups include halogens (bromine, chlorine, and iodine); oxygen-containing functional groups such as a hydroxyls, epoxides, carbonyls, aldehydes, ester, carboxyls, and acid chlorides; nitrogen-containing functional groups such as amines and azides; and sulfur-containing groups such as thiols. The functional group may also be a hydrocarbon moiety which contains one or more non-aromatic pi-bonds, such as an alkyne, alkene, or diene. Preferably, the branch point will contain at least two different types of functional groups (e.g., one or more alcohols and one or more carboxylic acids, or one or more halides and one or more alcohols). In such cases, the different functional groups present on the branch point can be independently addressed synthetically, permitting the covalent attachment of the hydrophobic and hydrophilic segments to the branch point in controlled stoichiometric ratios.

Following reaction of the hydrophobic and hydrophilic polymer segments with functional groups on the branch point, the one or more hydrophobic polymer segments and the one or more hydrophilic polymer segments will be covalently joined to the branch point via linking moieties. The identity of the linking moieties will be determined by the identity of the functional group and the reactive locus of the hydrophobic and hydrophilic polymer segments (as these elements react to form the linking moiety or a precursor of the linking moiety). Examples of suitable linking moieties that connect the polymer segments to the branch point include secondary amides (—CONH—), tertiary amides (—CONR—), secondary carbamates (—OCONH—; —NHCOO—), tertiary carbamates (—OCONR—; —NRCOO—), ureas (—NHCONH—; —NRCONH—; —NHCONR—, —NRCONR—), carbinols (—CHOH—, —CROH—), ethers (—O—), and esters (—COO—, —CH$_2$O$_2$C—, CHRO$_2$C—), wherein R is an alkyl group, an aryl group, or a heterocyclic group. In certain embodiments, the polymer segments are connected to the branch point via an ester (—COO—, —CH$_2$O$_2$C—, CHRO$_2$C—), a secondary amide (—CONH—), or a tertiary amide (—CONR—), wherein R is an alkyl group, an aryl group, or a heterocyclic group.

In certain embodiments, the branch point is polycarboxylic acid, such as citric acid, tartaric acid, mucic acid, gluconic acid, or 5-hydroxybenzene-1,2,3,-tricarboxylic acid. Exemplary branch points include the following organic compounds:

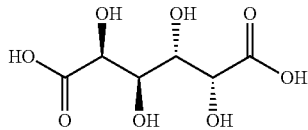

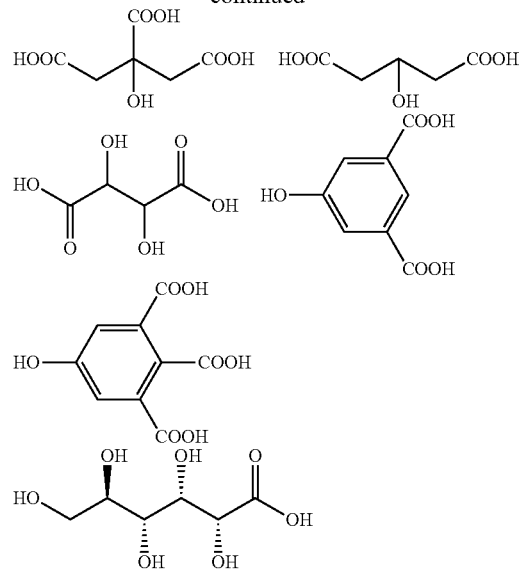

F. Synthesis of Polymer-Drug Conjugates

Polymer-drug conjugates can be prepared using synthetic methods known in the art. Representative methodologies for the preparation of polymer-drug conjugates are discussed below. The appropriate route for synthesis of a given polymer-drug conjugate can be determined in view of a number of factors, such as the structure of the polymer-drug conjugate, the identity of the polymers which make up the conjugate, the identity of the active agent, as well as the structure of the compound as a whole as it relates to compatibility of functional groups, protecting group strategies, and the presence of labile bonds.

In addition to the synthetic methodologies discussed below, alternative reactions and strategies useful for the preparation of the polymer-dug conjugates disclosed herein are known in the art. See, for example, March, "Advanced Organic Chemistry," 5$^{th}$ Edition, 2001, Wiley-Interscience Publication, New York).

Generally, polymer-drug conjugates are prepared by first forming the polymeric component of the polymer-drug conjugate, and then covalently attaching an active agent. For example, Schemes 1 and 2 illustrate the synthesis of a polymer-doxorubicin conjugate containing doxorubicin bound to a poly(sebacic anhydride) polymer segment to which is a single polyethylene glycol chain is attached (DXR-PSA-PEG).

Scheme 1:

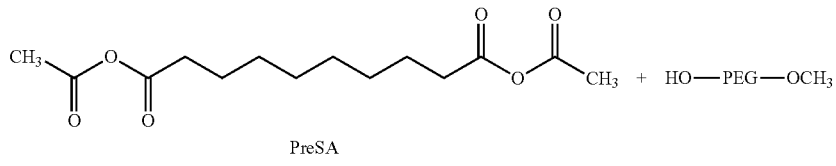

PreSA

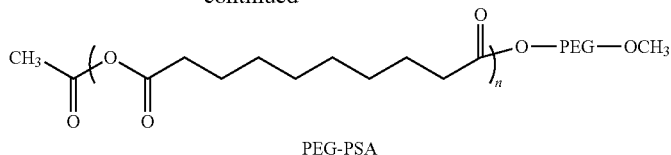

PEG-PSA

Scheme 2:

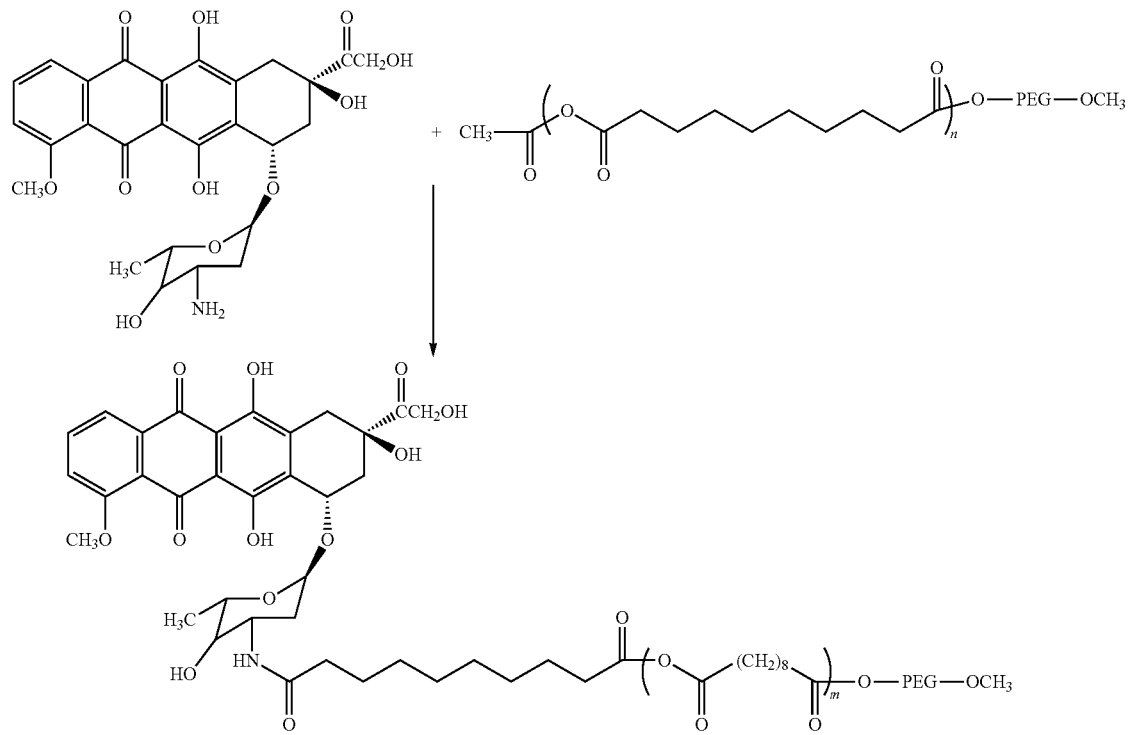

In a first step, sebacic acid is refluxed is acetic anhydride to form an acylated polysebacic acid precursor (PreSA). An excess of PreSA is then combined with polyethylene glycol methyl ether, and polymerized under anhydrous hot-melt polymerization conditions. As shown in Scheme 2, the resulting polymer (PEG-PSA) can then be reacted with doxorubicin to form the polymer-drug conjugate (DXR-PSA-PEG).

The synthesis of an exemplary polymer-drug conjugate containing multiple hydrophilic polymer segments (three PEG chains) attached to a hydrophobic polymer segment (poly(sebacic anhydride) via a branch point (citric acid) is described in Schemes 3 and 4.

In the case of polymer-drug conjugates containing a branch point, synthesis of the polymer drug conjugate will typically begin by sequentially attaching the hydrophobic polymer segment and the hydrophilic polymer segments to the branch point to form the polymeric portion of the polymer-drug conjugate. As shown in scheme 3, citric acid is first reacted with $CH_3O$-PEG-$NH_2$ in the presence of N,N-dicyclohexylcarbodiimide (DCC) and a catalytic amount of 4-dimethylaminopyridine (DMAP), forming amide linkages between the PEG chains and the three carboxylic acid residues of the citric acid branch point. The resulting compound is then reacted with an acylated polysebacic acid precursor (PreSA), and polymerized under anhydrous hot-melt polymerization conditions. As shown in Scheme 4, the resulting polymer ($PEG_3$-PSA) is then reacted with doxorubicin to form the polymer-drug conjugate (DXR-PSA-$PEG_3$).

Scheme 3:

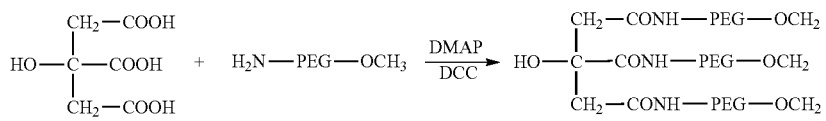

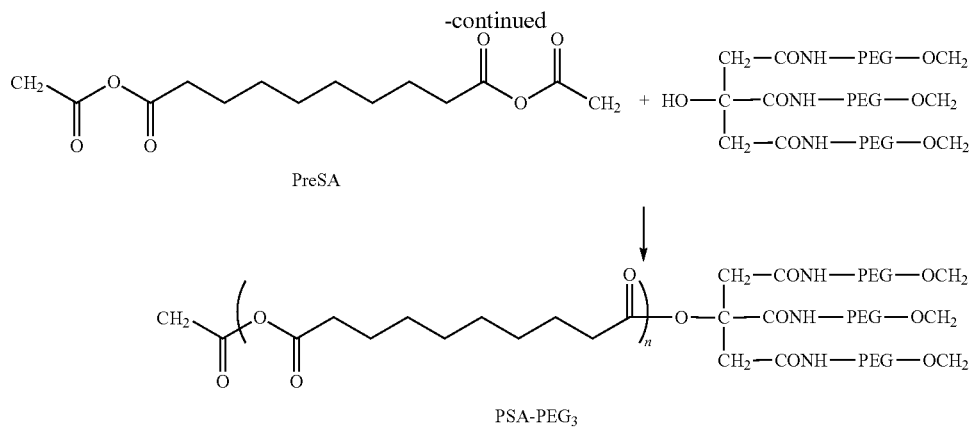

PreSA

PSA-PEG₃

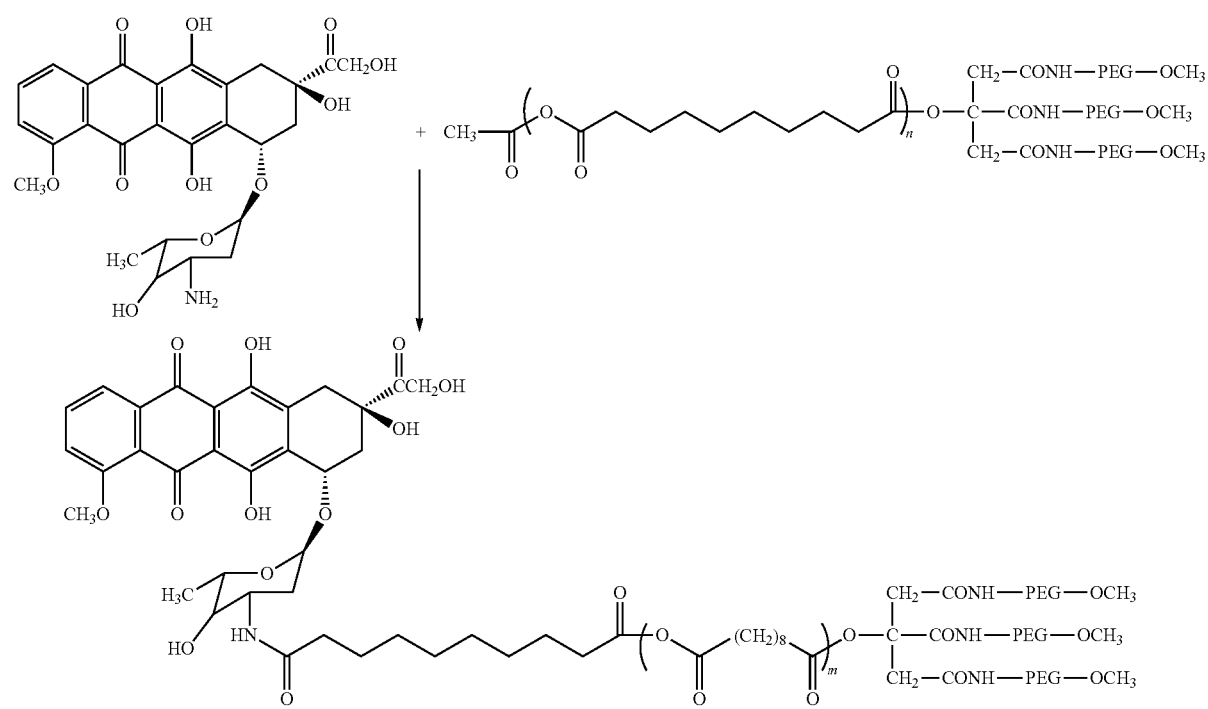

Scheme 4:

III. Particles and Implants for Controlled Delivery of HIF-1 Inhibitors

Polymeric implants (e.g., rods, discs, wafers, etc.), microparticles, and nanoparticles for the controlled delivery of one or more HIF-1 inhibitors are provided, either formed of the conjugates or having the conjugates dispersed or encapsulated in a matrix. In some embodiments, the particles or implants contain one or more HIF-1 inhibitors dispersed or encapsulated in a polymeric matrix. In preferred embodiments, the particles or implants are formed from polymer-drug conjugates containing one or more HIF-1 inhibitors that are covalently bound to a polymer.

A. Particles Formed from Polymer-Drug Conjugates

Microparticles and nanoparticles can be formed from one or more polymer-drug conjugates. In some cases, particles are formed from a single polymer-drug conjugate (i.e., the particles are formed from a polymer-drug conjugate which contains the same active agent, hydrophobic polymer segment, branch point (when present), and hydrophilic polymer segment or segments).

In other embodiments, the particles are formed from a mixture of two or more different polymer-drug conjugates. For example, particles may be formed from two or more polymer-drug conjugates containing different HIF-1 inhibitors and the same hydrophobic polymer segment, branch point (when present), and hydrophilic polymer segment or segments. Such particles can be used, for example, to co-administer two or more HIF-1 inhibitors. In other cases, the particles are formed from two or more polymer-drug conjugates containing the same HIF-1 inhibitor, and different hydrophobic polymer segments, branch points (when present), and/or hydrophilic polymer segments. Such particles can be used, for example, to vary the release rate of HIF-1 inhibitors. The particles can also be formed from two or more polymer-drug conjugates containing different HIF-1 inhibitors and different hydrophobic polymer segments, branch points (when present), and/or hydrophilic polymer segments.

Particles can also be formed from blends of polymer-drug conjugates with one or more additional polymers. In these cases, the one or more additional polymers can be any of the non-biodegradable or biodegradable polymers described in Section B below, although biodegradable polymers are preferred. In these embodiments, the identity and quantity of the one or more additional polymers can be selected, for example, to influence particle stability, i.e. that time required for distribution to the site where delivery is desired, and the time desired for delivery.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

In some embodiments, the population of particles formed from one or more polymer-drug conjugates is a monodisperse population of particles. In other embodiments, the population of particles formed from one or more polymer-drug conjugates is a polydisperse population of particles. In some instances where the population of particles formed from one or more polymer-drug conjugates is polydisperse population of particles, greater that 50%, 60%, 65%, 70%, 75%, 80%, 85%, 90%, or 95% of the particle size distribution lies within 10% of the median particle size.

Preferably, particles formed from one or more polymer-drug conjugates contain significant amounts of a hydrophilic polymer, such as PEG, on their surface.

B. Particles Containing One or More HIF-1 Inhibitors Dispersed in a Polymer Matrix Particles can also be formed containing one or more HIF-1 inhibitors dispersed or encapsulated in a polymeric matrix. The matrix can be formed of non-biodegradable or biodegradable matrices, although biodegradable matrices are preferred. The polymer is selected based on the time required for in vivo stability, i.e. that time required for distribution to the site where delivery is desired, and the time desired for delivery.

Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

Examples of preferred natural polymers include proteins such as albumin and prolamines, for example, zein, and polysaccharides such as alginate, cellulose and polyhydroxyalkanoates, for example, polyhydroxybutyrate. The in vivo stability of the matrix can be adjusted during the production by using polymers such as polylactide co glycolide copolymerized with polyethylene glycol (PEG). PEG if exposed on the external surface may elongate the time these materials circulate since it is hydrophilic.

Examples of preferred non-biodegradable polymers include ethylene vinyl acetate, poly(meth)acrylic acid, polyamides, copolymers and mixtures thereof.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. In certain embodiments, the particles are nanoparticles having a diameter of between 500 and 700 nm. The particles can have any shape but are generally spherical in shape.

C. Methods of Forming Microparticles and Nanoparticles

Microparticle and nanoparticles can be formed using any suitable method for the formation of polymer micro- or nanoparticles known in the art. The method employed for particle formation will depend on a variety of factors, including the characteristics of the polymers present in the polymer-drug conjugate or polymer matrix, as well as the desired particle size and size distribution. The type of HIF-1 inhibitor(s) being incorporated in the particles may also be a factor as some HIF-1 inhibitors are unstable in the presence of certain solvents, in certain temperature ranges, and/or in certain pH ranges.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

1. Solvent Evaporation

In this method, the polymer-drug conjugate (or polymer matrix and one or more HIF-1 inhibitors) is dissolved in a volatile organic solvent, such as methylene chloride. The organic solution containing the polymer-drug conjugate is then suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

Polymer-drug conjugates which contain labile polymers, such as certain polyanhydrides, may degrade during the fabrication process due to the presence of water. For these polymers, the following two methods, which are performed in completely anhydrous organic solvents, can be used.

2. Hot Melt Particle Formation

In this method, the polymer-drug conjugate (or polymer matrix and one or more HIF-1 inhibitors) is first melted, and then suspended in a non-miscible solvent (like silicon oil), and, with continuous stirring, heated to 5° C. above the melting point of the polymer-drug conjugate. Once the emulsion is stabilized, it is cooled until the polymer-drug conjugate particles solidify. The resulting nanoparticles are washed by decantation with a suitable solvent, such as petroleum ether, to give a free-flowing powder. The external surfaces of particles prepared with this technique are usually smooth and dense. Hot melt particle formation can be used to prepare particles containing polymer-drug conjugates which are hydrolytically unstable, such as certain polyanhydrides. Preferably, the polymer-drug conjugate used to prepare microparticles via this method will have an overall molecular weight of less than 75,000 Daltons.

3. Solvent Removal

Solvent removal can also be used to prepare particles from polymer-drug conjugates that are hydrolytically unstable. In this method, the polymer-drug conjugate (or polymer matrix and one or more HIF-1 inhibitors) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the polymer-drug conjugate.

4. Spray Drying

In this method, the polymer-drug conjugate (or polymer matrix and one or more HIF-1 inhibitors) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

5. Phase Inversion

Particles can be formed from polymer-drug conjugates using a phase inversion method. In this method, the polymer-drug conjugate (or polymer matrix and one or more HIF-1 inhibitors) is dissolved in a "good" solvent, and the solution is poured into a strong non solvent for the polymer-drug conjugate to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

6. Coacervation

Techniques for particle formation using coacervation are known in the art, for example, in GB-B-929 406; GB-B-929 40 1; and U.S. Pat. Nos. 3,266,987, 4,794,000, and 4,460, 563. Coacervation involves the separation of a polymer-drug conjugate (or polymer matrix and one or more HIF-1 inhibitors) solution into two immiscible liquid phases. One phase is a dense coacervate phase, which contains a high concentration of the polymer-drug conjugate, while the second phase contains a low concentration of the polymer-drug conjugate. Within the dense coacervate phase, the polymer-drug conjugate forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

7. Low Temperature Casting

Methods for very low temperature casting of controlled release microspheres are described in U.S. Pat. No. 5,019, 400 to Gombotz et al. In this method, the polymer-drug conjugate (or polymer matrix and one or more HIF-1 inhibitors) is dissolved in a solvent. The mixture is then atomized into a vessel containing a liquid non-solvent at a temperature below the freezing point of the polymer-drug conjugate solution which freezes the polymer-drug conjugate droplets. As the droplets and non-solvent for the polymer-drug conjugate are warmed, the solvent in the droplets thaws and is extracted into the non-solvent, hardening the microspheres.

D. Implants Formed from Polymer-Drug Conjugates

Implants can be formed from one or more polymer-drug conjugates. In preferred embodiments, the implants are intraocular implants. Suitable implants include, but are not limited to, rods, discs, wafers, and the like.

In some cases, the implants are formed from a single polymer-drug conjugate (i.e., the implants are formed from a polymer-drug conjugate which contains the same active agent, hydrophobic polymer segment, branch point (when present), and hydrophilic polymer segment or segments).

In other embodiments, the implants are formed from a mixture of two or more different polymer-drug conjugates. For example, implants may be formed from two or more polymer-drug conjugates containing different HIF-1 inhibitors and the same hydrophobic polymer segment, branch point (when present), and hydrophilic polymer segment or segments. Such implants can be used, for example, to co-administer two or more HIF-1 inhibitors. In other cases, the implants are formed from two or more polymer-drug conjugates containing the same HIF-1 inhibitor, and different hydrophobic polymer segments, branch points (when present), and/or hydrophilic polymer segments. Such implants can be used, for example, to vary the release rate of HIF-1 inhibitors. The implants can also be formed from two or more polymer-drug conjugates containing different HIF-1 inhibitors and different hydrophobic polymer segments, branch points (when present), and/or hydrophilic polymer segments.

Implants can also be formed from a polymeric matrix having one or more HIF-1 inhibitors dispersed or encapsulated therein. The matrix can be formed of any of the non-biodegradable or biodegradable polymers described in Section B above, although biodegradable polymers are preferred. The composition of the polymer matrix is selected based on the time required for in vivo stability, i.e. that time required for distribution to the site where delivery is desired, and the time desired for delivery.

Implants can also be formed from blends of polymer-drug conjugates with one or more of the polymers described in Section B above.

1. Implant Size and Shape

The implants may be of any geometry such as fibers, sheets, films, microspheres, spheres, circular discs, rods, or plaques. Implant size is determined by factors such as toleration for the implant, location of the implant, size limitations in view of the proposed method of implant insertion, ease of handling, etc.

Where sheets or films are employed, the sheets or films will be in the range of at least about 0.5 mm×0.5 mm, usually about 3 to 10 mm×5 to 10 mm with a thickness of about 0.1 to 1.0 mm for ease of handling. Where fibers are employed, the fiber diameter will generally be in the range of about 0.05 to 3 mm and the fiber length will generally be in the range of about 0.5 to 10 mm.

The size and shape of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Intraocular implants may be spherical or non-spherical in shape. For spherical-shaped implants, the implant may have a largest dimension (e.g., diameter) between about 5 μm and about 2 mm, or between about 10 μm and about 1 mm for administration with a needle, greater than 1 mm, or greater than 2 mm, such as 3 mm or up to 10 mm, for administration by surgical implantation. If the implant is non-spherical, the implant may have the largest dimension or smallest dimension be from about 5 μm and about 2 mm, or between about 10 μm and about 1 mm for administration with a needle, greater than 1 mm, or greater than 2 mm, such as 3 mm or up to 10 mm, for administration by surgical implantation.

The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg. In some embodiments, the dimension are, or are similar to, implants already approved for intraocular injection via needle: diameter of 460 microns and a length of 6 mm and diameter of 370 microns and length of 3.5 mm.

Intraocular implants may also be designed to be least somewhat flexible so as to facilitate both insertion of the implant in the eye, such as in the vitreous, and subsequent accommodation of the implant. The total weight of the implant is usually about 250 to 5000 μg, more preferably about 500-1000 μg. In certain embodiments, the intraocular implant has a mass of about 500 μg, 750 μg, or 1000 μg.

2. Methods of Manufacture

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymer segments present in the implant, the properties of the one or more HIF-1 inhibitors present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymer segments and HIF-1 inhibitor are chosen so as to be stable at the temperatures required for manufacturing, usually at least about 85 degrees Celsius. However, depending on the nature of the polymeric components and the one or more HIF-1 inhibitors, extrusion methods can employ temperatures of about 25 degrees Celsius to about 150 degrees Celsius, more preferably about 65 degrees Celsius to about 130 degrees Celsius.

Implants may be coextruded in order to provide a coating covering all or part of the surface of the implant. Such coatings may be erodible or non-erodible, and may be impermeable, semi-permeable, or permeable to the HIF-1 inhibitor, water, or combinations thereof. Such coatings can be used to further control release of the HIF-1 inhibitor from the implant.

Compression methods may be used to make the implants. Compression methods frequently yield implants with faster release rates than extrusion methods. Compression methods may employ pressures of about 50-150 psi, more preferably about 70-80 psi, even more preferably about 76 psi, and use temperatures of about 0 degrees Celsius to about 115 degrees Celsius, more preferably about 25 degrees Celsius.

IV. Pharmaceutical Formulations

Pharmaceutical formulations contain one or more polymer-drug conjugates in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

In some cases, the pharmaceutical formulation contains only one type of conjugate or polymeric particles for the controlled release of HIF-1 inhibitors (e.g., a formulation containing polymer-drug conjugate particles wherein the polymer-drug conjugate particles incorporated into the pharmaceutical formulation have the same composition). In other embodiments, the pharmaceutical formulation contains two or more different type of conjugates or polymeric particles for the controlled release of HIF-1 inhibitors (e.g., the pharmaceutical formulation contains two or more populations of polymer-drug conjugate particles, wherein the populations of polymer-drug conjugate particles have different chemical compositions, different average particle sizes, and/or different particle size distributions).

A. Additional Active Agents

In addition to the one or more HIF-1 inhibitors present in the polymeric particles, the formulation can contain one or more additional therapeutic, diagnostic, and/or prophylactic agents. The active agents can be a small molecule active agent or a biomolecule, such as an enzyme or protein, polypeptide, or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be encapsulated in, dispersed in, or otherwise associated with particles formed from one or more polymer-drug conjugates. In certain embodiments, one or more additional active agents may also be dissolved or suspended in the pharmaceutically acceptable carrier.

In the case of pharmaceutical compositions for the treatment of ocular diseases, the formulation may contain one or more ophthalmic drugs. In particular embodiments, the ophthalmic drug is a drug used to treat, prevent or diagnose a disease or disorder of the posterior segment eye. Non-limiting examples of ophthalmic drugs include anti-glaucoma agents, anti-angiogenesis agents, anti-infective agents, anti-inflammatory agents, growth factors, immunosuppressant agents, anti-allergic agents, and combinations thereof.

Representative anti-glaucoma agents include prostaglandin analogs (such as travoprost, bimatoprost, and latanoprost),beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., parasympathomimetics, such as pilocarpine and ecothiopate), seretonergics muscarinics, dopaminergic agonists, and adrenergic agonists (such as apraclonidine and brimonidine).

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and corticosteroids.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

B. Formulations for Ocular Administration

Particles formed from the polymer-drug conjugates will preferably be formulated as a solution or suspension for injection to the eye.

Pharmaceutical formulations for ocular administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

V. Methods of Use

Controlled release dosage formulations for the delivery of one or more HIF-1 inhibitors can be used to treat or a disease or disorder in a patient associated with vascularization, including cancer and obesity. In preferred embodiment, the pharmaceutical compositions are administered to treat or prevent a disease or disorder in a patient associated with ocular neovascularization. Upon administration, the one or more HIF-1 inhibitors are released over an extended period of time at concentrations which are high enough to produce therapeutic benefit, but low enough to avoid cytotoxicity.

When administered to the eye, the particles release a low dose of one or more active agents over an extended period of time, preferably longer than 3, 7, 10, 15, 21, 25, 30, or 45 days. The structure of the polymer-drug conjugate or makeup of the polymeric matrix, particle morphology, and dosage of particles administered can be tailored to administer a therapeutically effective amount of one or more active agents to the eye over an extended period of time while minimizing side effects, such as the reduction of scoptopic ERG b-wave amplitudes and/or retinal degeneration.

A. Diseases and Disorders of the eye

Pharmaceutical compositions containing particles for the controlled release of one or more HIF-1 inhibitors can be administered to the eye of a patient in need thereof to treat or prevent one or more diseases or disorders of the eye. In some cases, the disease or disorder of the eye affects the posterior segment of the eye. The posterior segment of the eye, as used herein, refers to the back two-thirds of the eye, including the anterior hyaloid membrane and all of the optical structures behind it, such as the vitreous humor, retina, choroid, and optic nerve.

In preferred embodiments, a pharmaceutical composition containing particles formed from one or more of the polymer-drug conjugates provided herein is administered to treat or prevent an intraocular neovascular disease. In certain embodiments, the particles are formed from a polymer-drug conjugate containing an anthracycline, such as daunorubicin or doxorubicin.

Eye diseases, particularly those characterized by ocular neovascularization, represent a significant public health concern. Intraocular neovascular diseases are characterized by unchecked vascular growth in one or more regions of the eye. Unchecked, the vascularization damages and/or obscures one or more structures in the eye, resulting in vision loss. Intraocular neovascular diseases include proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, central retinal vein occlusion (CRVO), corneal neovascularization, and retinal neovascularization (RNV). Intraocular neovascular diseases afflict millions worldwide, in many cases leading to severe vision loss and a decrease in quality of life and productivity.

Age related macular degeneration (AMD) is a leading cause of severe, irreversible vision loss among the elderly. Bressler, et al. JAMA, 291:1900-1901 (2004). AMD is characterized by a broad spectrum of clinical and pathologic findings, such as pale yellow spots known as drusen, disruption of the retinal pigment epithelium (RPE), choroidal neovascularization (CNV), and disciform macular degeneration. AMD is classified as either dry (i.e., non-exudative) or wet (i.e., exudative). Dry AMD is characterized by the presence of lesions called drusen. Wet AMD is characterized by neovascularization in the center of the visual field.

Although less common, wet AMD is responsible for 80%-90% of the severe visual loss associated with AMD (Ferris, et al. Arch. Ophthalmol. 102:1640-2 (1984)). The cause of AMD is unknown. However, it is clear that the risk of developing AMD increases with advancing age. AMD has also been linked to risk factors including family history, cigarette smoking, oxidative stress, diabetes, alcohol intake, and sunlight exposure.

Wet AMD is typically characterized by CNV of the macular region. The choroidal capillaries proliferate and penetrate Bruch's membrane to reach the retinal pigment epithelium (RPE). In some cases, the capillaries may extend into the subretinal space. The increased permeability of the newly formed capillaries leads to accumulation of serous fluid or blood under the RPE and/or under or within the neurosensory retina. Decreases in vision occur when the fovea becomes swollen or detached. Fibrous metaplasia and organization may ensue, resulting in an elevated subretinal mass called a disciform scar that constitutes end-stage AMD and is associated with permanent vision loss (D'Amico D J. N. Engl. J. Med. 331:95-106 (1994)).

Other diseases and disorders of the eye, such as uveitis, are also difficult to treat using existing therapies. Uveitis is a general term referring to inflammation of any component of the uveal tract, such as the iris, ciliary body, or choroid. Inflammation of the overlying retina, called retinitis, or of the optic nerve, called optic neuritis, may occur with or without accompanying uveitis.

Ocular complications of uveitis may produce profound and irreversible loss of vision, especially when unrecognized or treated improperly. The most frequent complications of uveitis include retinal detachment, neovascularization of the retina, optic nerve, or iris, and cystoid macular edema. Macular edema (ME) can occur if the swelling, leaking, and background diabetic retinopathy (BDR) occur within the macula, the central 5% of the retina most critical to vision. ME is a common cause of severe visual impairment.

There have been many attempts to treat intraocular neurovascular diseases, as well as diseases associated with chronic inflammation of the eye, with pharmaceuticals. Attempts to develop clinically useful therapies have been plagued by difficulty in administering and maintaining a therapeutically effective amount of the pharmaceutical in the ocular tissue for an extended period of time. In addition, many pharmaceuticals exhibit significant side effects and/or toxicity when administered to the ocular tissue.

Intraocular neovascular diseases are diseases or disorders of the eye that are characterized by ocular neovascularization. The neovascularization may occur in one or more regions of the eye, including the cornea, retina, choroid layer, or iris. In certain instances, the disease or disorder of the eye is characterized by the formation of new blood vessels in the choroid layer of the eye (i.e., choroidal neovascularization, CNV). In some instances, the disease or disorder of the eye is characterized by the formation of blood vessels originating from the retinal veins and extending along the inner (vitreal) surface of the retina (i.e., retinal neovascularization, RNV).

Exemplary neovascular diseases of the eye include age-related macular degeneration associated with choroidal neovascularization, proliferative diabetic retinopathy (diabetic retinopathy associated with retinal, preretinal, or iris neovascularization), proliferative vitreoretinopathy, retinopathy of prematurity, pathological myopia, von Hippel-Lindau disease, presumed ocular histoplasmosis syndrome (POHS), and conditions associated with ischemia such as branch retinal vein occlusion, central retinal vein occlusion, branch retinal artery occlusion, and central retinal artery occlusion.

The neovascularization can be caused by a tumor. The tumor may be either a benign or malignant tumor. Exemplary benign tumors include hamartomas and neurofibromas. Exemplary malignant tumors include choroidal melanoma, uveal melanoma or the iris, uveal melanoma of the ciliary body, retinoblastoma, or metastatic disease (e.g., choroidal metastasis).

The neovascularization may be associated with an ocular wound. For example, the wound may the result of a traumatic injury to the globe, such as a corneal laceration. Alternatively, the wound may be the result of ophthalmic surgery.

The polymer-drug conjugates can be administered to prevent or reduce the risk of proliferative vitreoretinopathy following vitreoretinal surgery, prevent corneal haze following corneal surgery (such as corneal transplantation and eximer laser surgery), prevent closure of a trabeculectomy, or to prevent or substantially slow the recurrence of pterygii.

The polymer-drug conjugates can be administered to treat or prevent an eye disease associated with inflammation. In such cases, the polymer-drug conjugate preferably contains an anti-inflammatory agent. Exemplary inflammatory eye diseases include, but are not limited to, uveitis, endophthalmitis, and ophthalmic trauma or surgery.

The eye disease may also be an infectious eye disease, such as HIV retinopathy, toxocariasis, toxoplasmosis, and endophthalmitis.

Pharmaceutical compositions containing particles formed from one or more of the polymer-drug conjugates can also be used to treat or prevent one or more diseases that affect other parts of the eye, such as dry eye, meibomitis, glaucoma, conjunctivitis (e.g., allergic conjunctivitis, vernal conjunctivitis, giant papillary conjunctivitis, atopic keratoconjunctivitis), neovascular glaucoma with iris neovascularization, and iritis.

1. Methods of Administration a. Mode of Administration

The formulations described herein can be administered locally to the eye by intravitreal injection (e.g., front, mid or back vitreal injection), subconjunctival injection, intracameral injection, injection into the anterior chamber via the temporal limbus, intrastromal injection, injection into the subchoroidal space, intracorneal injection, subretinal injection, and intraocular injection. In a preferred embodiment, the pharmaceutical composition is administered by intravitreal injection.

The implants described herein can be administered to the eye using suitable methods for implantation known in the art. In certain embodiments, the implants are injected intravitreally using a needle, such as a 22-gauge needle. Placement of the implant intravitreally may be varied in view of the implant size, implant shape, and the disease or disorder to be treated.

In some embodiments, the pharmaceutical compositions and/or implants described herein are co-administered with one or more additional active agents. "Co-administration", as used herein, refers to administration of the controlled release formulation of one or more HIF-1 inhibitors with one or more additional active agents within the same dosage form, as well as administration using different dosage forms simultaneously or as essentially the same time. "Essentially at the same time" as used herein generally means within ten minutes, preferably within five minutes, more preferably within two minutes, most preferably within in one minute.

In some embodiments, the pharmaceutical compositions and/or implants described herein are co-administered with one or more additional treatments for a neovascular disease or disorder of the eye. In some embodiments, the pharmaceutical compositions and/or implants described herein are co-administered with one or more anti-angiogenesis agent such bevacizumab (AVASTIN®), ranibizumab, LUCENTIS®, or aflibercept (EYLEA®).

b. Dosage

Preferably, the particles will release an effective amount of one or more HIF-1 inhibitors over an extended period of time. In preferred embodiments, the particles release an effective amount of one or more HIF-1 inhibitors over a period of at least two weeks, more preferably over a period of at least four weeks, more preferably over a period of at least six weeks, most preferably over a period of at least eight weeks. In some embodiments, the particles release an effective amount of one or more HIF-1 inhibitors over a period of three months or longer.

In some cases, a pharmaceutical formulation is administered to a patient in need thereof in a therapeutically effective amount to decrease choroidal neovascularization. In some cases, a pharmaceutical formulation is administered to a patient in need thereof in a therapeutically effective amount to decrease retinal neovascularization.

c. Therapeutic Efficacy

In the case of age-related macular degeneration, therapeutic efficacy in a patient can be measured by one or more of the following: assessing the mean change in the best corrected visual acuity (BCVA) from baseline to a desired time, assessing the proportion of patients who lose fewer than 15 letters (three lines) in visual acuity at a desired time as compared to a baseline, assessing the proportion of patients who gain greater than or equal to 15 letters (three lines) in visual acuity at a desired time as compared to a baseline, assessing the proportion of patients with a visual acuity Snellen equivalent of 20/2000 or worse at a desired time, assessing the National Eye Institute Visual Functioning Questionnaire, and assessing the size of CNV and the amount of leakage of CNV at a desired time using fluorescein angiography.

In certain embodiments, at least 25%, more preferably at least 30%, more preferably at least 35%, most preferably at least 40% of the patients with recent onset CNV who are treated with the formulations described herein improve by three or more lines of vision.

B. Other Diseases and Disorders

Controlled release dosage formulations for the delivery of one or more HIF-1 inhibitors can be used to treat or a disease or disorder in a patient associated with vascularization, including cancer and obesity.

The present invention will be further understood by reference to the following non-limiting examples.

EXAMPLES

Example 1: Preparation of Polyanhydride-Drug Conjugate Particles Synthesis of Polymer (Polyethylene glycol)$_3$-co-poly(sebacic acid) (PEG$_3$-PSA) was prepared by melt polycondensation. Briefly, sebacic acid was refluxed in acetic anhydride to form a sebacic acid prepolymer (Acyl-SA). Citric-Polyethylene glycol (PEG$_3$) was prepared using methods known in the art (Ben-Shabat, S. et al. *Macromol. Biosci.* 6:1019-1025 (2006)). 2.0 g of CH$_3$O-PEG-NH$_2$, 26 mg of citric acid, 83 mg of dicyclohexylcarbodiimide (DCC), and 4.0 mg of 4-(dimethylamino)pyridine (DMAP) were added to 10 mL of methylene chloride. This mixture was stirred overnight at room temperature, then precipitated, washed with ether, and dried under vacuum to isolate PEG$_3$. Next, Acyl-SA (90% w/w) and PEG$_3$ (10% w/w) were polymerized at 180° C. for 30 minutes. Nitrogen gas was swept into the flask for 30 seconds every 15 minutes. The reaction was allowed to proceed for 30 min. Polymers were cooled to ambient temperature, dissolved in chloroform, and precipitated into excess petroleum ether. The precipitate was collected by filtration and dried under vacuum to constant weight.

Formation of DXR-PSA-PEG$_3$ Nanoparticles

DXR-PSA-PEG$_3$ nanoparticles were prepared by dissolving PEG$_3$-PSA with DXR at defined ratios in 3 mL dichloromethane and 1 mL DMSO and reacting for 2 hrs at 50° before homogenizing (L4RT, Silverson Machines, East Longmeadow, Mass.) into 100 mL of an aqueous solution containing 1% polyvinyl alcohol (25 kDa, Sigma). Particles were then hardened by allowing chloroform to evaporate at room temperature while stirring for 2 hours. The particles were collected by centrifugation (20,000×g for 20 min at 4° C.), and washed thrice with double distilled water. Particle size was determined by dynamic light scattering using a ZetaSizer Nano ZS (Malvern Instruments, Southborough, Mass.). Size measurements were performed at 25° C. at a scattering angle of 90°.

DXR Release from DXR-PSA-PEG$_3$ Nanoparticles In Vitro

DXR-PSA-PEG$_3$ nanoparticles were suspended in phosphate buffered saline (PBS, pH 7.4) at 2 mg/mL and incubated at 37° C. on a rotating platform (140 RPM). At selected time points, supernatant was collected by centrifugation (13,500×g for 5 min) and particles were resuspended in fresh PBS. DXR content was measured by absorbance at 480 nm.

Results

The DXR-PSA-PEG$_3$ nanoparticles prepared above contained 23.6% DXR (by weight), and had an average particle size of 647 nm. In vitro studies showed that DXR was released from the nanoparticles as a conjugate with sebacic acid in a steady fashion for up to two weeks under sink conditions in PBS at 37° C. with no initial rapid drug release phase (i.e., no "burst effect").

Example 2: Treatment of Choroidal Neovascularization in a Mouse Model of CNV Materials and Methods Pathogen-free C57BL/6 mice (Charles River, Wilmington, Mass.) were treated in accordance with the Association for Research in Vision and Ophthalmology Statement for the Use of Animals in Ophthalmic and Vision Research and the guidelines of the Johns Hopkins University Animal Care and Use Committee.

Choroidal NV was induced by laser photocoagulation-induced rupture of Bruch's membrane as previously described (Tobe, T. et al., Am. J. Pathol. 135(5): 1641-1646 (1998)). Briefly, 5-6-week-old female C57BL/6 mice were anesthetized with ketamine hydrochloride (100 mg/kg body weight) and pupils were dilated. Laser photocoagulation (75 μm spot size, 0.1 sec duration, 120 mW) was performed in the 9, 12, and 3 o'clock positions of the posterior pole of each eye with the slit lamp delivery system of an OcuLight GL diode laser (Iridex, Mountain View, Calif.) and a hand-held cover slip as a contact lens to view the retina. Production of a bubble at the time of laser, which indicates rupture of Bruch's membrane, is an important factor in obtaining CNV; therefore, only burns in which a bubble was produced were included in the study.

Immediately after laser-induced rupture of Bruch's membrane, mice were randomized to various treatment groups for intraocular injections. Intravitreal injections were done under a dissecting microscope with a Harvard Pump Micro-injection System and pulled glass micropipettes.

At 1, 4, 7, and 14 days after injection, fundus photographs were taken with a Micron III® camera (Phoenix Research Laboratories Inc., Pleasanton, Calif.). After 14 days, the mice were perfused with 1 ml of PBS containing 25 mg/ml of fluorescein-labeled dextran (2×10$^6$ Daltons average molecular weight; Sigma-Aldrich, St. Louis, Mo.) and choroidal flat mounts were examined by fluorescence microscopy. Images were captured with a Nikon Digital Still Camera DXM1200 (Nikon Instruments Inc., New York, N.Y.). Image analysis software (Image-Pro® Plus; Media Cybernetics, Silver Spring, Md.) was used to measure the total area of CNV at each rupture site with the investigator masked with respect to treatment group.

Treatment of Oxygen-Induced Ischemic Retinopathy

C57BL/6 mice placed in 75% oxygen at postnatal day (P) 7 and at P12 were returned to room air and given an intraocular injection of PBS or PBS containing Daunorubicin, Doxorubicin, or DXR-PSA-PEG$_3$ nanoparticles. At P17, the area of retinal NV on the surface of the retina was measured. Briefly, P17 mice were given an intraocular injection of 1 μl of rat anti-mouse platelet endothelial cell adhesion molecule-1 (PECAM-1) antibody (Pharmingen, San Jose, Calif.) and after 12 hours they were euthanized and eyes were fixed in PBS-buffered formalin for 5 hours at room temperature. Retinas were dissected, washed, and incubated with goat-anti rat polyclonal antibody conjugated with Alexa 488 (Invitrogen, Carlsbad, Calif.) at 1:500 dilution at room temperature for 45 minutes and flat mounted. An observer masked with respect to treatment group measured the area of NV per retina by image analysis.

Treatment of VEGF-Induced Retinal Neovascularization

Hemizygous rhodopsin/VEGF transgenic mice that express VEGF in photoreceptors were given an intraocular injection of 1 μl of PBS or PBS containing 10 ug DXR-PSA-PEG$_3$ nanoparticles at P14. At P21, P28, P35, P42 or P49, the mice were anesthetized, perfused with fluorescein-labeled dextran (2×10$^6$ average molecular weight, Sigma- Aldrich), and retinal flat mounts were examined by fluorescence microscopy (Axioskop2 plus; Zeiss, Thornwood, N.Y.) at 400× magnification, which provides a narrow depth of field, so that when neovascularization along the outer edge of the retina is brought into focus, the remainder of the retinal vessels are out of focus, allowing easy delineation and quantification of the neovascularization. Images were digitized with a three-color charge-coupled device video camera (Cool SNAP™-Pro; Media Cybernetics, Silver Spring, Md.) and a frame grabber. Image analysis software (Image-Pro Plus 5.0; Media Cybernetics, Silver Spring, Md.) was set to recognize fluorescently stained neovascularization and used to calculate the total area of neovascularization per retina. The investigator performing image analysis was masked with respect to treatment group.

Recording of Electroretinograms (ERGs)

Adult C57BL/6 mice were given an intraocular injection of 1 µl of PBS or PBS containing of 0.1, 1.0, or 10 µg of Daunorubicin or Doxorubicin, or 1.0 or 10 µg DXR-PSA-PEG$_3$ nanoparticles. Scotopic and photopic ERGs were recorded at one, seven and 14 days after injection using an Espion ERG Diagnosys machine. For scotopic recordings, mice were dark adapted overnight, and for photopic recordings, mice were adapted for 10 min to background white light at an intensity of 30 cd/m$^2$. The mice were anesthetized with an intraperitoneal injection of ketamine hydrochloride (100 mg/kg body weight) and xylazine (5 mg/kg body weight). Pupils were dilated with Midrin P containing of 0.5% tropicamide and 0.5% phenylephrine, hydrochloride (Santen Pharmaceutical Co., Osaka, Japan). The mice were placed on a pad heated to 39° C. and platinum loop electrodes were placed on each cornea after application of Gonioscopic prism solution (Alcon Labs, Fort Worth, Tex.). A reference electrode was placed subcutaneously in the anterior scalp between the eyes and a ground electrode was inserted into the tail. The head of the mouse was held in a standardized position in a ganzfeld bowl illuminator that ensured equal illumination of the eyes. Recordings for both eyes were made simultaneously with electrical impedance balanced. Scotopic ERGs were recorded at 11 intensity levels of white light ranging from −3.00 to 1.40 log cd-s/m2. Six measurements were averaged for each flash intensity. Photopic ERGs were recorded at three intensity levels of white light ranging from 0.60 to 1.40 log cd-s/m2 with a 30 cd/m2 background. Five measurements were averaged for each flash intensity.

Measurement of Outer Nuclear Layer (ONL) Thickness

ONL thickness was measured. Adult C57BL/6 mice were given an intraocular injection of 1 µl of PBS or PBS containing of 0.1, 1.0, or 10 µg of Daunorubicin or Doxorubicin, or 1.0 or 10 µg DXR-PSA-PEG$_3$ nanoparticles. Mice were euthanized, a mark was placed at 12:00 at the corneal limbus, and eyes were removed and embedded in optimal cutting temperature compound. Ten micrometer frozen sections were cut parallel to the 12:00 or 9:00 meridian through the optic nerve and fixed in 4% paraformaldehyde. The sections were stained with hematoxylin and eosin, examined with an Axioskop microscope (Zeiss, Thornwood, N.Y.), and images were digitized using a three charge-coupled device (CCD) color video camera (IK-TU40A; Toshiba, Tokyo, Japan) and a frame grabber. Image-Pro Plus software (Media Cybernetics, Silver Spring, Md.) was used to outline the ONL. With the observer masked with respect to treatment group, ONL thickness was measured at six locations, 25% (S1), 50% (S2), and 75% (S3) of the distance between the superior pole and the optic nerve and 25% (I1), 50% (I2), and 75% (I3) of the distance between the inferior pole the optic nerve.

Statistical Analysis

Data were expressed as mean±SEM. Statistical analysis was performed using Student's t-test and P<0.05 was considered significant.

Results

Anthracyclines Suppress Choroidal and Retinal NV

Figure 1B:
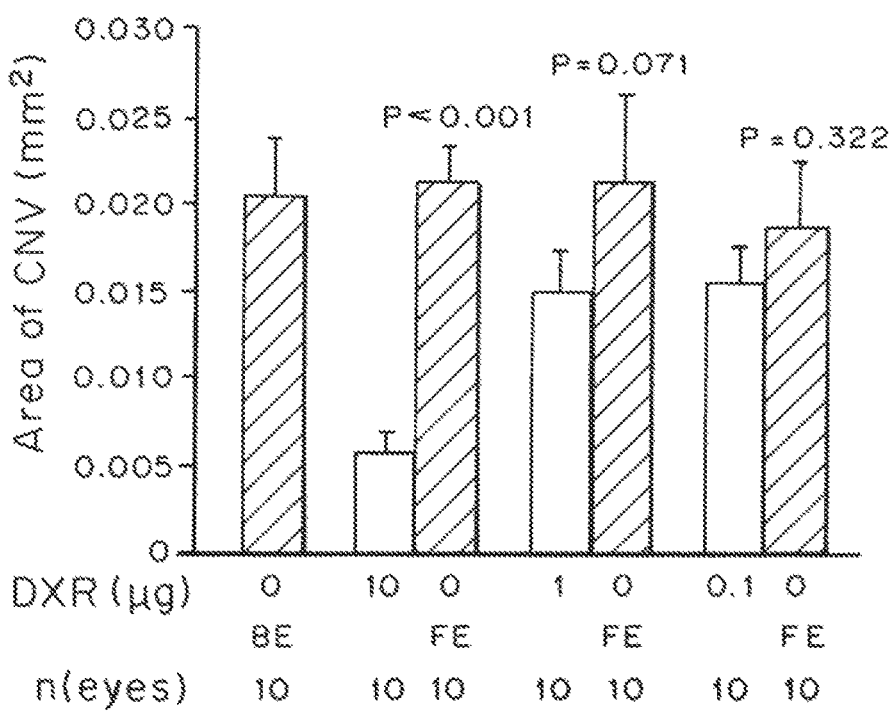

In a mouse model of choroidal NV (Tobe, T. et al. *Am. J. Pathol.* 153:1641-1646 (1998)) that is predictive of drug effects in patients with neovascular AMD (Saishin, Y. et al. *J. Cell Physiol.* 195:241-248 (2003)), intraocular injection of 10 µg of DNR suppressed choroidal NV, while injection of 1 or 0.1 µg had no significant effect (FIG. 1A). Similarly, intraocular injection of 10 µg of DXR suppressed choroidal NV and injections of 1 or 0.1 µg did not have a significant effect (FIG. 1B).

Figure 2A:
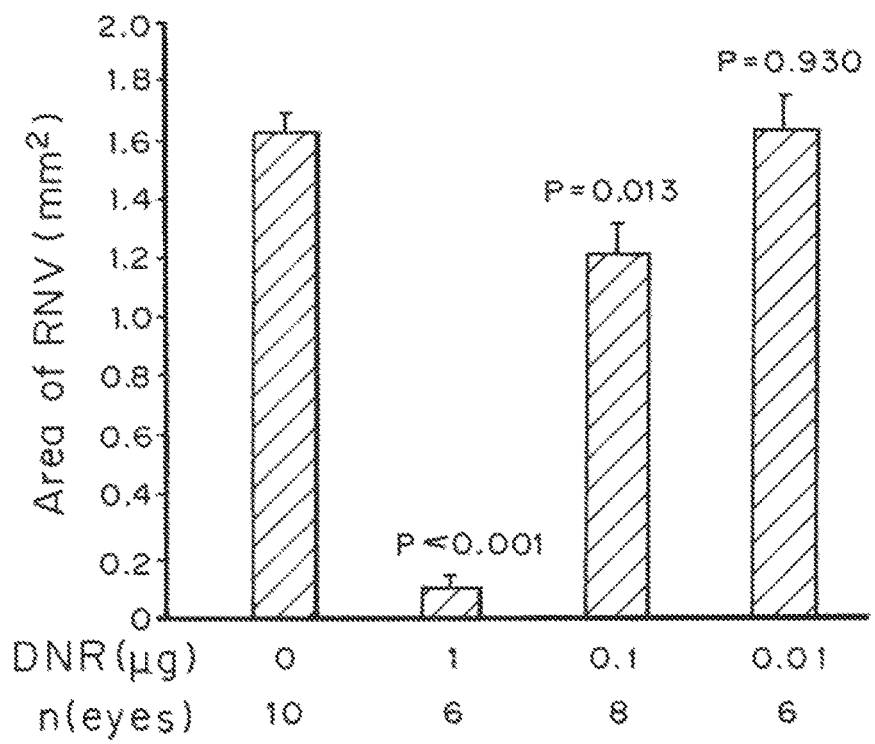
FIGS. 2A-B are bar graphs plotting the area of retinal neovascularization (RNV) (in $mm^2$) observed in the eyes of C57BL/6 mice with oxygen-induced ischemic retinopathy five days after the administration of a vehicle control (PBS buffer without a HIF-1 inhibitor present), and upon administration of varying amounts of doxorubicin or daunorubicin. The bars represent the mean (±SEM) area of RNV.
Figure 2B:
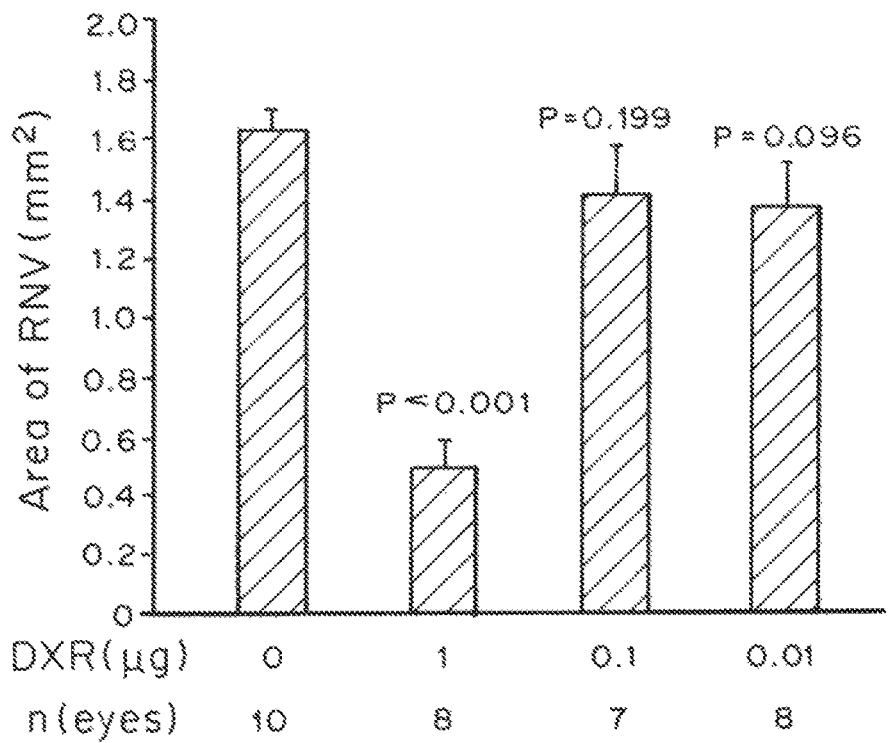

In neonatal mice with oxygen-induced ischemic retinopathy, a model predictive of effects in proliferative diabetic retinopathy, intraocular injection of 1 µg of DNR markedly reduced the area of retinal NV, 0.1 µg caused a small reduction, and 0.01 µg had no significant effect (FIG. 2A). The NV was visualized on retinal flat mounts after in vivo immunofluorescent staining with anti-PECAM1, a technique that selectively stains NV and hyaloid vessels. Intraocular injection of 1 µg of DXR, but not 0.1 or 0.01 µg, significantly reduced the area of retinal NV (FIG. 2B). Five days after injection of 1 µg of DNR or DXR, precipitated drug was visualized on the surface of the retina. The mean area of choroidal or retinal NV in fellow eyes was not significantly different from that in eyes of mice in which both eyes were injected with vehicle indicating that there was no systemic effect from intraocular injections of DNR or DXR.

Effect of Intraocular Injections of DNR or DXR on Retinal Function

Since DNR and DXR are antimetabolites as well as HIF-1 inhibitors we examined their effect on retinal function assessed by ERGs. Fourteen days after intraocular injections of 1 µg, but not 0.1 µg, of DNR or DXR there was a significant reduction in mean scotopic and photopic b-wave amplitudes. These data indicate that while DNR and DXR strongly suppress ocular NV, bolus injections of free drugs can cause retinal toxicity.

Retinal Toxicity After Intraocular Injection of Digoxin

It has been previously demonstrated that intraocular injections of 0.01-0.25 µg of digoxin suppress HIF-1 transcriptional activity and ocular NV (Yoshida, T. et al. *FASEB J.* 24:1759-1767 (2010)). To explore whether the deleterious effects of DXR and DNR on retinal function might be related to their suppression of HIF-1 activity, the effects of intraocular injection of 0.25 and 0.05 µg of digoxin on retinal function were measured. One week after intraocular injection of 0.25 µg of digoxin, there was a significant reduction in mean scotopic a-wave amplitude, mean scotopic b-wave amplitude, and mean photopic b-wave amplitude. There was also a reduction in outer nuclear layer thickness at 3 of 6 measurement locations in the retina, indicating death of photoreceptor cells. These results are consistent with substantial toxicity after intraocular injection of 0.25 µg of digoxin. Intraocular injection of 0.05 µg of digoxin was less toxic, but still caused significant reduction in mean scotopic and photopic b-wave amplitudes. Thus, for both anthracyclines and digoxin, injection of free drug into the eye carries risk of retinal toxicity.

Effect of DXR-Polymer Nanoparticles on Ocular NV

The effect of intraocular injection of DXR nanoparticles was first tested in mice with laser-induced choroidal NV. After laser-induced rupture of Bruch's membrane, C57BL/6 mice received an intraocular injection of 10, 1, or 0.1 µg of DXR-PSA-PEG$_3$ nanoparticles. Fundus photos of the animals that received 1 µg of DXR-PSA-PEG$_3$ nanoparticles showed a large orange mass of nanoparticles overlying the posterior retina 1 day after injection that decreased slowly over time and was still readily visible on day 14. Particles remained visible over periods of time as long as five weeks.

Figure 3A:
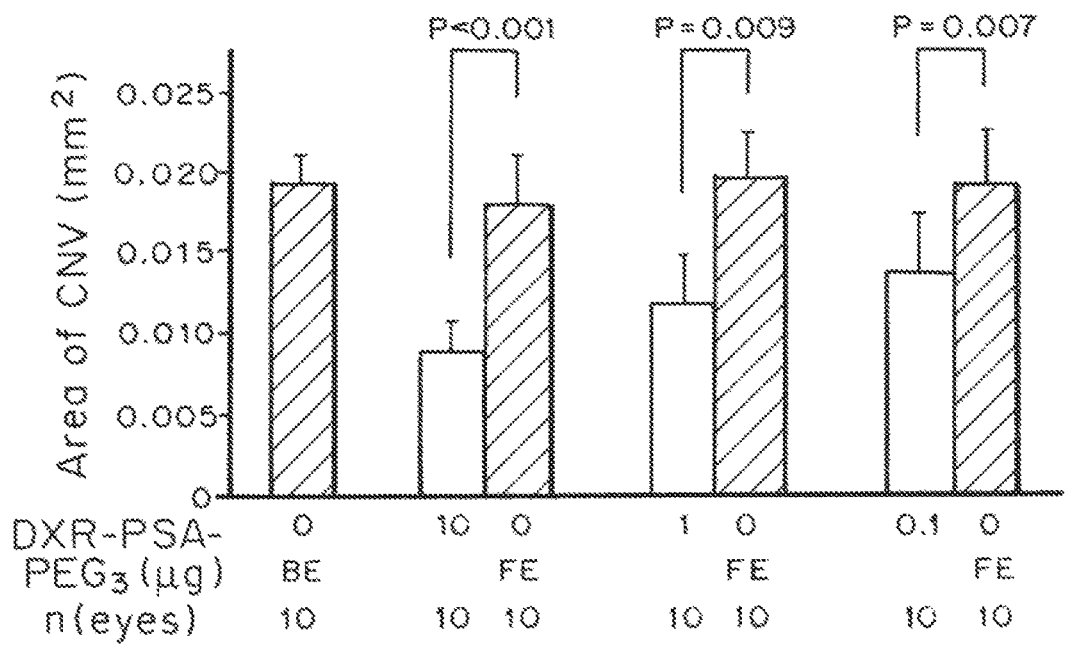
FIG. 3A is a graph demonstrating the efficacy of a controlled-release formulation of a HIF-1 inhibitor (specifically DXR-PSA-PEG$_3$ nanoparticles) in treating CNV in a mouse model of CNV.

In mice perfused with fluorescein-labeled dextran to visualize choroidal NV by fluorescence microscopy at day 14, the area of choroidal NV appeared smaller in eyes given an intraocular injection of DXR-PSA-PEG$_3$ nanoparticles compared to fellow eyes injected with PBS. Image analysis confirmed that compared to eyes injected with PBS, the mean area of choroidal NV was significantly less in eyes injected with 10, 1, or 0.1 µg of DXR-PSA-PEG$_3$ nanoparticles (FIG. 3A).

Figure 3B:
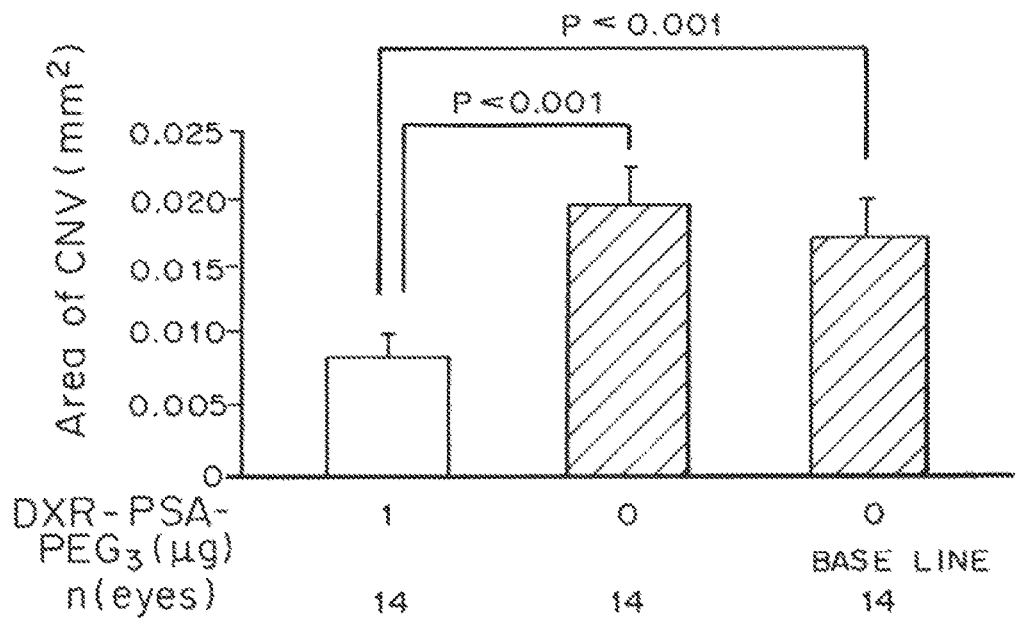
FIG. 3B is a graph demonstrating the efficacy of a controlled-release formulation of a HIF-1 inhibitor (specifically DXR-PSA-PEG$_3$ nanoparticles) in treating established CNV in a mouse model of CNV. In this case, the Bruch's membrane of C57BL/6 mice were ruptured by laser photocoagulation, and CNV was allowed to grow for a period of seven days. Subsequently, one cohort had the baseline area of CNV measured, and the remaining mice were treated by injection of 1 µg of DXR-PSA-PEG$_3$ nanoparticles in one eye, and injection of vehicle only in the fellow eye. After an additional seven days, the area of CNV was measured in the DXR-PSA-PEG$_3$ and vehicle-treated eyes.

The effect of DXR-PSA-PEG$_3$ nanoparticles on already established choroidal NV was investigated by allowing the NV to grow for 7 days and then injecting 1 µg of DXR-PSA-PEG$_3$ nanoparticles. Seven days after injection, eyes injected with DXR-PSA-PEG$_3$ nanoparticles had a mean area of choroidal NV that was significantly less than that seen in control eyes injected with PBS, and also significantly less than the baseline amount of choroidal NV that was present at 7 days (FIG. 3B). This indicates that DXR-PSA-PEG$_3$ nanoparticles cause regression of established choroidal NV.

Figure 4:
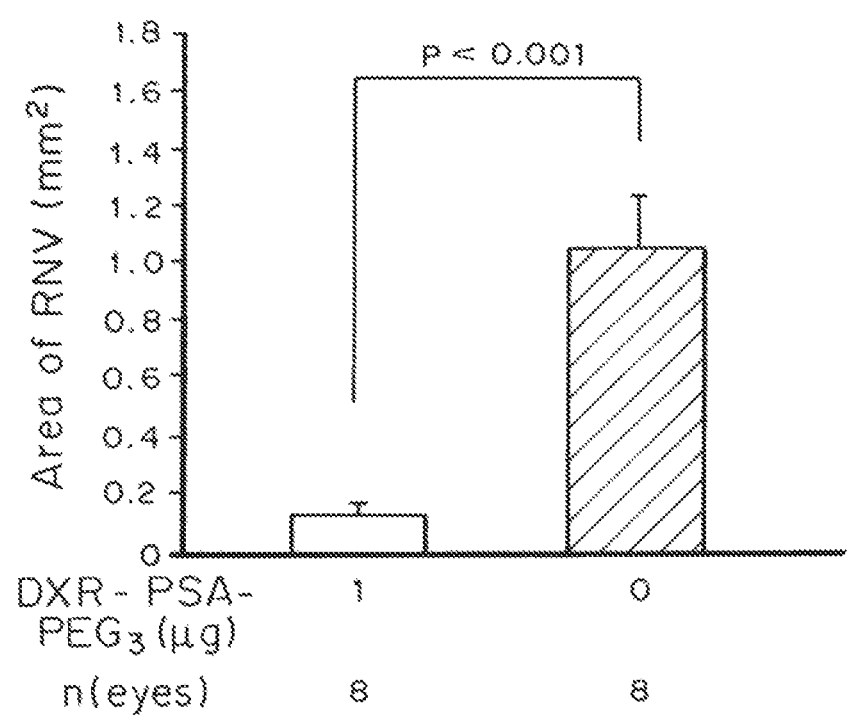
FIG. 4 is a graph demonstrating the efficacy of a controlled-release formulation of a HIF-1 inhibitor (specifically DXR-PSA-PEG$_3$ nanoparticles) in treating RNV in mice with oxygen-induced ischemic retinopathy.

The DXR-PSA-PEG$_3$ nanoparticle formulation was also investigated using a model of ischemia-induced retinal neovascularization (Smith, L. E. H. et al. *Invest. Ophthalmol. Vis. Sci.* 35:101-111 (1994)). Intraocular injections of 1 µg of DXR-PSA-PEG$_3$ nanoparticles significantly reduced the mean area of retinal NV compared to fellow eyes injected with PBS (FIG. 4).

Prolonged Suppression of NV After Intraocular Injection of DXR Polymer Nanoparticles in rho/VEGF Transgenic Mice Rho/VEGF transgenic mice, in which the rhodopsin promoter drives expression of VEGF in photoreceptors, have sustained expression of VEGF starting at postnatal day (P) 7, and provide an excellent model to test the duration of activity of a therapeutic agent (Okamoto, N. et. al. *Am. J. Pathol.* 151:281-291 (1997)).

Figure 5A:
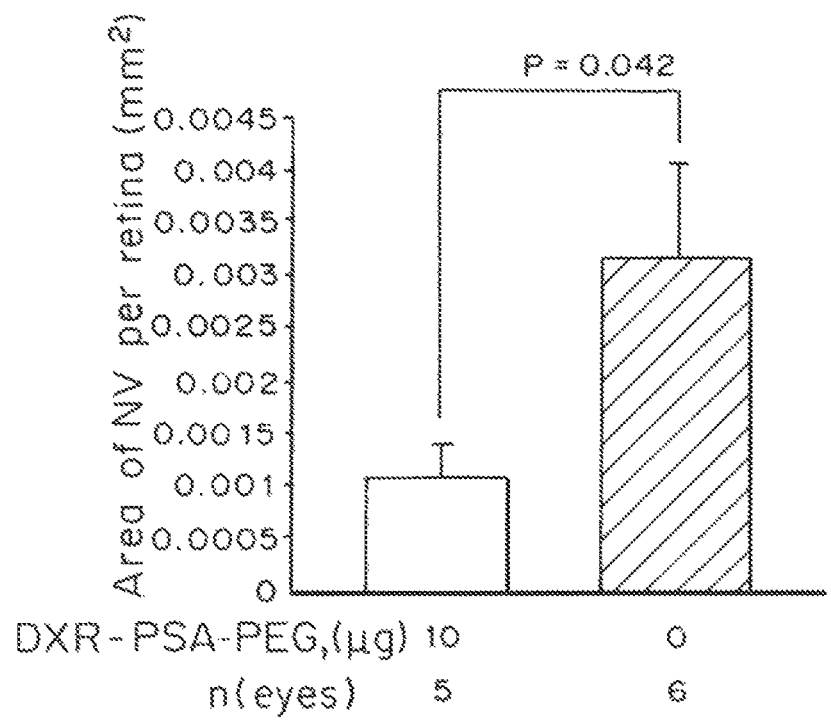
FIGS. 5A-B are bar graphs demonstrating the ability of controlled-release formulation of a HIF-1 inhibitor (specifically DXR-PSA-PEG$_3$ nanoparticles) to suppress subretinal neovascularization (NV) in transgenic mice in which the rhodopsin promoter drives expression of VEGF in photoreceptors (rho/VEGF mice) for at least 35 days. At postnatal day (P) 14, hemizygous rho/VEGF mice were given an intraocular injection of 10 µg of DXR-PSA-PEG$_3$ nanoparticles in one eye and vehicle only (PBS buffer) in the fellow eye.
Figure 5B:
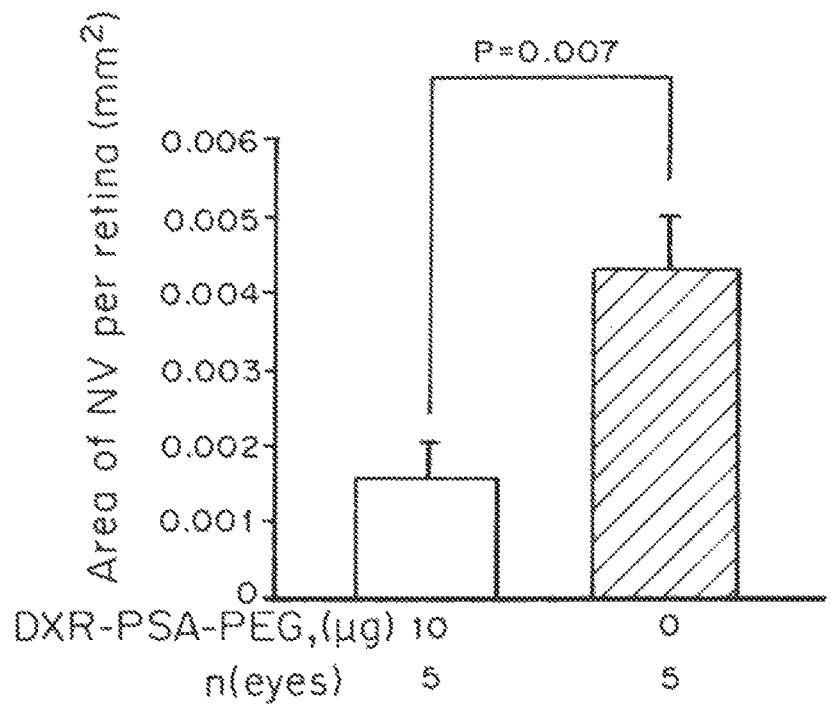

At P14, hemizygous rho/VEGF mice were given an intraocular injection of 10 µg of DXR-PSA-PEG$_3$ nanoparticles in one eye and PBS in the fellow eye. At 4 (FIG. 5A) or 5 weeks (FIG. 5B), the mean area of subretinal NV was significantly less in DXR nanoparticle-injected eyes than vehicle-injected fellow eyes.

Intraocular Injection of 1 or 10 µg of DXR Nanoparticles Did Not Cause Toxicity as Measured by ERG or ONL Thickness At 14 days after intraocular injection of 10 µg of DXR-PSA-PEG$_3$, there was no significant difference in scotopic or photopic b-wave amplitudes compared to PBS-injected eyes. There was also no difference in outer nuclear layer thickness indicating that DXR nanoparticles did not cause photoreceptor cell death.

Example 3: Pharmacokinetic Study in Rabbits

Materials and Methods

Preparation of the PEG$_3$-PSA Polymer (Polyethylene glycol)3-co-poly(sebacic acid) (PEG3-PSA) was synthesized by melt condensation. Briefly, sebacic acid was refluxed in acetic anhydride to form sebacic acid prepolymer (Acyl-SA). Polyethylene glycol (PEG$_3$) was prepared by mixing CH3O-PEG-NH2 (2.0 g), citric acid (26 g), dicyclohexylcarbodiimide (DCC; 83 mg) and 4-(dimethylamino)pyridine (DMAP, 4.0 mg) which were added to 10 mL methylene chloride, stirred overnight at room temperature, then precipitated and washed with ether, and dried under vacuum. Next, acyl-SA (90% w/w) and PEG$_3$ (10% w/w) were polymerized at 180° C. for 30 mins. Nitrogen gas was swept into the flask for 30 seconds every 15 minutes. Polymers were cooled to ambient temperature, dissolved in chloroform and precipitated into excess petroleum ether. The precipitate was collected by filtration and dried under vacuum to constant weight, to produce the PEG3-PSA polymer.

Preparation of the DXR-PSA-PEG$_3$ Nanoparticles and Microparticles

To prepare DXR-PSA-PEG$_3$ nanoparticles, 80 mg PEG$_3$-PSA was dissolved in 6 mL dichloromethane (DCM) and 20 mg doxorubicin hydrochloride (DXR) (NetQem LLC, Durham, N.C.) was dissolved in 2 mL dimethylsulfoxide (DMSO). The solutions of polymer and drug were mixed and kept at 50° C. for 30 min. The resulting mixture was homogenized in 50 mL of 1% polyvinyl alcohol (PVA) solution (25 kDa, Polyscience, Niles, Ill.) at 10,000 rpm for 3 min using a L4RT homogenizer (Silverson Machines, East Longmeadow, Mass.). The particle suspension was stirred at room temperature for 2 hours to remove dichloromethane. The particles were collected by centrifugation (20,000×g for 20 minutes at 4° C.) and washed thrice with ultrapure water prior to lyophilization.

DXR-PSA-PEG$_3$ microparticles were prepared in a similar fashion. Briefly, 200 mg PEG$_3$-PSA was dissolved in 3 mL DCM and mixed with 40 mg DXR dissolved in 1.5 mL DMSO. Following incubation at 50° C. for 30 min, the mixture was homogenized in 100 mL of PVA at 3,000 rpm for 1 min. After stirring for 2 hr, particles were collected by centrifugation (9,000×g for 25 minutes) and washed thrice before lyophilization.

Particle Characterization

Particle size was determined using a Coulter Multisizer IV (Beckman-Coulter Inc., Fullerton, Calif.). Greater than 100,000 particles were sized for each batch of microparticles to determine the mean particle diameter. Particle morphology was characterized by scanning electron microscopy (SEM) using a cold cathode field emission SEM (JEOL JSM-6700F, Peabody, Mass.). Drug loading was determined by dissolving dry powder of the particles in DCM and DMSO and the absorbance was measured using a UV spectrophotometer at 490 nm.

Animal Procedures

Pigmented, Dutch-Belted rabbits were used for these studies (n=10). Animals were treated in accordance with the Association for Research in Vision and Ophthalmology Statement of Use of Animals in Ophthalmic and Research and the guidelines of the Johns Hopkins University Animal Care and Use Committee. For intraocular injections and collection of aqueous humor, animals were anesthetized with an intramuscular injection of ketamine (25 mg/kg) and xylazine (2.5 mg/Kg). When sedated, the pupils were dilated with 2.5% phenylephrine hydrochloride and 10% tropicamide. Ocular surface anesthesia was performed using topical instillation of 0.5% proparacaine hydrochloride.

For the injections, a 26-gauge needle was carefully introduced into the vitreous cavity, 1.5 mm posterior to the superotemporal limbus, with the needle tip directed into the mid-vitreous. A volume of 0.1 mL of GB-AMD-101 micro or nanoparticle suspension was delivered to the right eyes, and 0.1 mL vehicle (PBS) was delivered to the left eyes. The needle was held in place for 10 seconds before withdrawal to prevent reflux from the entry site. Animals were returned to their cages and monitored until anesthesia was reversed.

At the indicated times, aqueous humor was withdrawn (~0.1 mL) by inserting a 30-gauge needle through the limbus and removing the aqueous humor. The samples were stored at −80° C. until use. At the end of the study (Day 105 for the nanoparticle-treated animals and Day 115 for the microparticle-treated animals), animals were euthanized using a pentobarbital-based euthanasia (>150 mg/Kg). Animals were enucleated and vitreous was isolated and stored at −80° C. until use.

HPLC Quantitation of Released Drug Conjugate in Rabbit Aqueous Humor and Vitreous Samples Prior to quantitation of the drug content by HPLC, 100 µL of aqueous humor sample or vitreous sample was mixed with 200 µL of methanol and incubated at 4° C. for 3 hr. After centrifugation (15,000×g, 10 min) and filtration through a 0.2 µm PTFE filter, 150 µL of the filtrate was injected into a Waters HPLC system equipped with a c18 reverse phase column (5 µm, 4.6×250 mm; Grace, Deerfield Ill.). Released drug conjugate was eluted by an isocratic mobile phase containing water and acetonitrile (60%:40%, v/v) at 1 mL/min and detected using a fluorescence detector (excitation wavelength: 500 nm, emission wavelength: 551 nm). The estimated limit of detection was 10 ng/mL. A series of DXR aqueous solutions at different concentrations were used as calibration standards. The data was analyzed using Empower 3 chromatography data software (Waters Corporation, Milford Mass.).

Results

DXR-PSA-PEG$_3$ Microparticles and Nanoparticles

Microparticles and nanoparticles composed of the DXR-SA-PEG$_3$ conjugate were synthesized and characterized as described. Particles were sized prior to lyophilization and following reconstitution in vehicle (PBS). The microparticles displayed a mean size of 27.2+1.0 um, and the nanoparticles, 0.98+0.02 um prior to lyophilization (Table 1; FIG. 6). The average drug loading of the microparticles was 13% and the nanoparticles was 20% (Table 1).

TABLE 1

Characterization of DXR-PSA-PEG$_3$ Micro and Nanoparticles

| Type | Sample ID Prior to lyophilization | Particle Diameter by Volume Post-reconstitution in PBS | Average Drug Loading (w/w) |
|---|---|---|---|
| Microparticles | 27.2 ± 10.4 µm | 24.3 ± 8.3 µm | 13% |
| Nanoparticles | 0.98 ± 0.74 µm | 3.7 ± 2.0 µm | 20% |

Figure 6A:
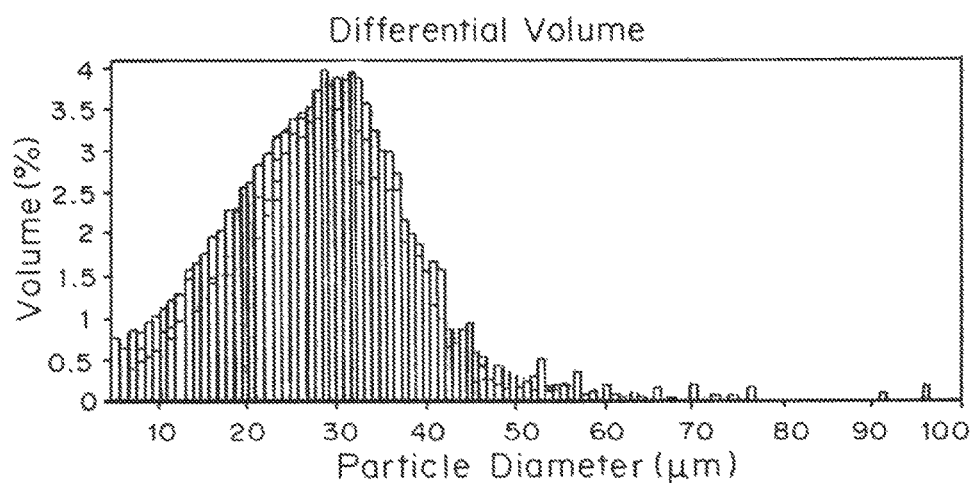
FIG. 6A is a graph showing the size distribution by volume of microparticles as determined using a Coulter Multisizer.
Figure 6B:
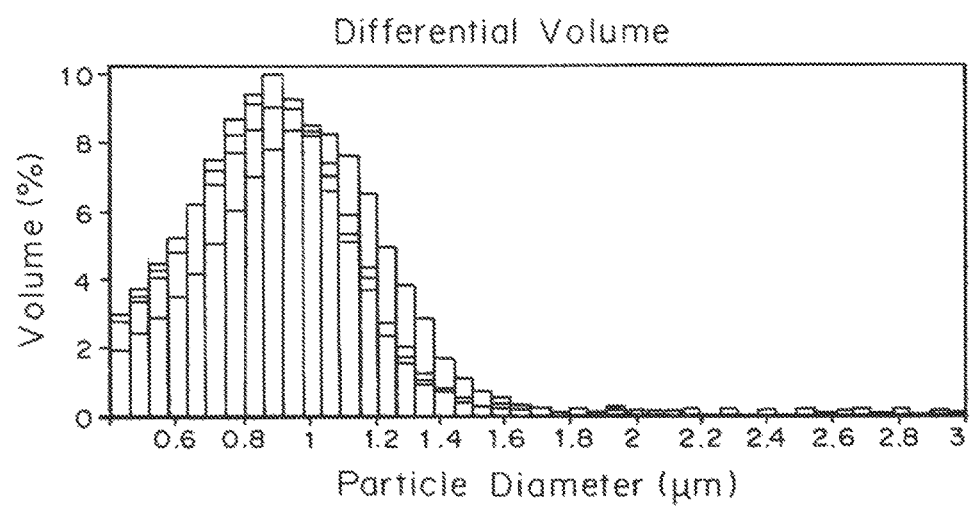
FIG. 6B is a graph showing the size distribution by volume of nanoparticles as determined using a Coulter Multisizer.

SEM analyses demonstrated discrete particles of the expected size. FIGS. 6A and 6B show the size distribution by volume of the microparticles and nanoparticles, respectively.

Duration of Drug Release Following IVT Administration to Rabbits

Rabbits received an intravitreal injection (0.1 mL) of the DXR-PSA-PEG$_3$ microparticles or nanoparticles into their right eyes and vehicle alone (PBS) into their left eyes. At the indicated times, aqueous humor was collected (~0.1 mL) and analyzed for the presence of released drug conjugate using a quantitative HPLC-based assay. On Day 115 (microparticle group) or Day 105 (nanoparticle group), animals were euthanized and aqueous humor and vitreous was collected. The released drug levels in the AH were compared to that in the vitreous for each animal.

Figure 7A:
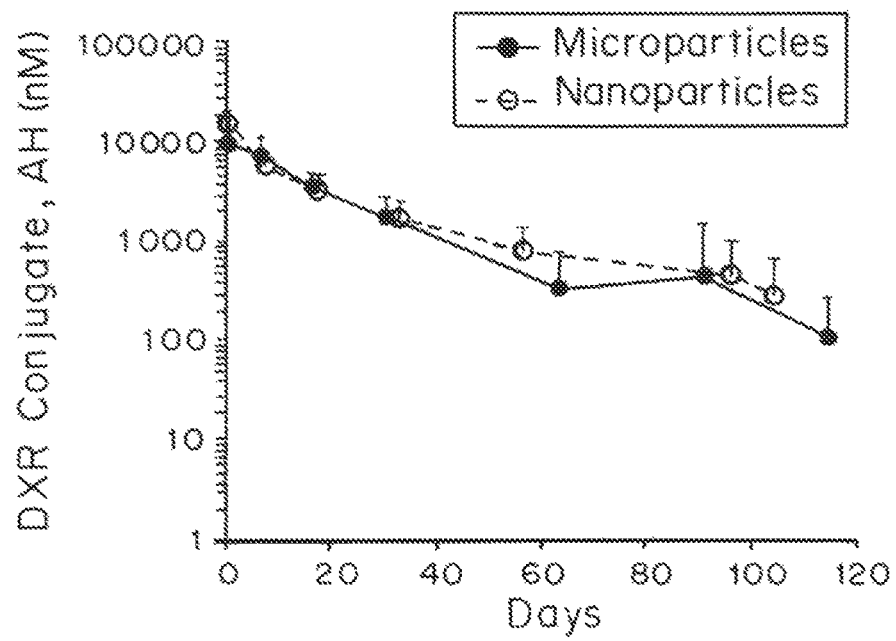
FIG. 7A is a graph showing the amount of drug conjugate released (nM) into the aqueous humor (AH) as a function of time (days) from microparticles and nanoparticles injected into the eyes of rabbits.

All rabbits displayed sustained drug release following intravitreal particle administration (FIG. 7A, Table 2).

TABLE 2

Pharmacokinetics of Intravitreal Delivery of DXR-PSA-PEG$_3$ Particles to Rabbits.

| DXR-PSA-PEG$_3$ Microparticles | | DXR-PSA-PEG$_3$ Nanoparticles | |
|---|---|---|---|
| Day | DXR Conc. in Aqueous Humor | Day | DXR Conc. in Aqueous Humor |
| 1 | 4.74 ± 2.23 µg/mL | 1 | 6.91 ± 2.40 µg/mL |
| 7 | 3.45 ± 1.76 µg/mL | 8 | 2.61 ± 1.11 µg/mL |
| 17 | 1.63 ± 0.65 µg/mL | 18 | 1.51 ± 0.77 µg/mL |
| 31 | 0.78 ± 0.52 µg/mL | 33 | 0.75 ± 0.41 µg/mL |
| 64 | 0.16 ± 0.21 µg/mL | 57 | 0.37 ± 0.27 µg/mL |
| 92 | 0.21 ± 0.45 µg/mL | 97 | 0.22 ± 0.26 µg/mL |
| 115 | 0.05 ± 0.08 µg/mL | 105 | 0.13 ± 0.18 µg/mL |

Data presented as mean ± SD.

Levels well above the limit of quantitation of the HPLC assay (10 ng/mL or 20 nM) were observed in the AH of both the microparticle and nanoparticle-treated animals for the duration of the study, 115 and 105 days, respectively (FIG. 7A). Direct comparison of the released drug levels in the AH compared to the vitreous revealed that vitreous levels were significantly higher than those measured in the AH, up to 188 times higher in the vitreous compared to the AH (Table 3, FIG. 7B). The mean released drug levels for the microparticle-treated animals at Day 115 were 0.09+0.13 uM in the AH and 7.12+12.92 uM in the vitreous. For the nanoparticle-treated animals at Day 105 mean released drug levels were 0.23+0.31 uM in the AH and 11.91+10.45 uM in the vitreous (Table 3). Drug levels in the vitreous were 77-90 times higher than drug levels measured in the AH.

Figure 7B:
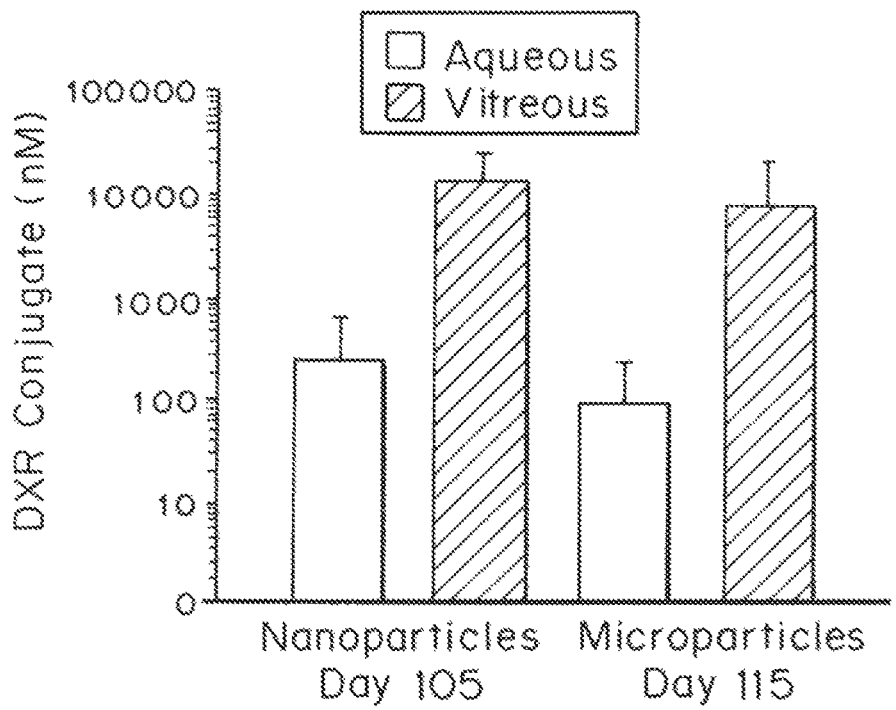
FIG. 7B is a bar graph that compares the amounts of released DXR drug conjugate (nM) in the aqueous humor (AH) and the vitreous of particle-injected rabbit eyes. The time (days) is 105 for the nanoparticle-treated animals and 115 for the microparticle-treated animals.

FIG. 7A is a graph showing the amount of released DXR drug conjugate (nM) as a function of time (days) in the aqueous humor (AH) of rabbits treated with microparticles and nanoparticles injected into the vitreous. FIG. 7B is a bar graph comparing the released drug amounts in the aqueous humor (AH) and vitreous of nanoparticle and microparticle-treated rabbits at days 105 and 115, respectively.

TABLE 3

Comparison of Released Drug Levels in the Aqueous Humor vs Vitreous

| Treatment | DXR concentration | | | | Ratio (uM) |
| --- | --- | --- | --- | --- | --- |
| | Aqueous Humor | | Vitreous | | |
| | ug/mL | uM | ug/mL | uM | Vitreous/Aqueous |
| Microparticles | | | | | |
| Rabbit 1 | 0.020 | 0.034 | 0.34 | 0.59 | 17 |
| Rabbit 2 | 0.184 | 0.317 | 17.50 | 30.17 | 95 |
| Rabbit 3 | 0.014 | 0.024 | 1.75 | 3.01 | 125 |
| Rabbit 4 | 0.030 | 0.052 | 0.79 | 1.37 | 27 |
| Rabbit 5 | 0.002 | 0.004 | 0.27 | 0.47 | 122 |
| Mean | 0.05 ± 0.08 | 0.09 ± 0.13 | 4.13 ± 7.50 | 7.12 ± 12.92 | 77 ± 52 |
| Nanoparticles | | | | | |
| Rabbit 1 | 0.10 | 0.17 | 4.81 | 8.30 | 50 |
| Rabbit 2 | 0.06 | 0.10 | 1.65 | 2.84 | 29 |
| Rabbit 3 | 0.45 | 0.77 | 17.32 | 29.86 | 39 |
| Rabbit 4 | 0.03 | 0.06 | 6.31 | 10.88 | 188 |
| Rabbit 5 | 0.03 | 0.05 | 4.44 | 7.66 | 144 |
| Mean | 0.13 ± 0.18 | 0.23 ± 0.31 | 6.91 ± 6.06 | 11.91 ± 10.45 | 90 ± 72 |

Data presented as mean ± SD.

Intravitreal delivery of DXR-PSA-PEG$_3$ micro or nanoparticles to rabbit eyes resulted in long-term drug release, sustained for at least 115 or 105 days, respectively, the duration of the study. The released drug levels measured in the vitreous where much higher than those measured in the aqueous humor, an average of 77-90-fold higher.

These data demonstrate sustained release from of DXR-PSA-PEG$_3$ when delivered intraocularly and suggest that of DXR-PSA-PEG$_3$ will be a promising therapy for the treatment of NV ocular diseases including NV AMD.

Example 4: Synthesis and In Vitro Evaluation of Fully Biodegradable of DXR-PSA-PEG$_3$ Rods Rod-shaped of DXR-PSA-PEG$_3$ were successfully produced with a diameter of 0.5 mm, a length of 0.5 cm, and a mass of 1 mg, with three doxorubicin (DXR) drug loading levels, 10%, 30%, and 50%. DXR conjugate release in vitro demonstrated release sustained for at least 25 days with all three rod types.

Materials and Methods
Preparation of PEG$_3$-PSA Polymer (Polyethylene glycol)$_3$-co-poly(sebacic acid) (PEG$_3$-PSA) was synthesized by melt condensation. Briefly, sebacic acid was refluxed in acetic anhydride to form sebacic acid prepolymer (Acyl-SA). Polyethylene glycol (PEG$_3$) was prepared by mixing CH$_3$O-PEG-NH$_2$ (2.0 g), citric acid (26 g), dicyclohexylcarbodiimide (DCC; 83 mg) and 4-(dimethylamino)pyridine (DMAP, 4.0 mg) which were added to 10 mL methylene chloride, stirred overnight at room temperature, then precipitated and washed with ether, and dried under vacuum. Next, acyl-SA (90% w/v) and PEG$_3$ (10% w/v) were polymerized at 180° C. for 30 minutes. Nitrogen gas was swept into the flask every 30 seconds for 15 minutes. Polymers were cooled to ambient temperature, dissolved in chloroform and precipitated into excess petroleum ether. The precipitate was collected by filtration and dried under vacuum to constant weight, to produce the PEG$_3$-PSA polymer.

Preparation of DXR-PSA-PEG$_3$ Rod

To prepare of DXR-PSA-PEG$_3$ rods, three different concentrations of DXR were used to produce rods with drug loading levels of 10%, 30% and 50% (w/w). For the 10%, 30% and 50% drug loaded rods, PEG$_3$-PSA and doxorubicin hydrochloride (DXR) (NetQem LLC, Durham, N.C.) were added to CHCl$_3$ at ratios of 9:1, 7:3, and 1:1 (w/w). The PEG$_3$-PSA and DXR were incubated at 50° C. for one hour after which the CHCl$_3$ was removed by vacuum. The reaction product was grated to a fine powder and then compressed into a glass tube, with a diameter of 0.5 mm, which was used as a mold. The rods were extruded from the mold and cut to 0.5 cm lengths. Each rod weighed approximately 1 mg (0.9-1.2 mg).

In Vitro Drug Release

One rod (~1 mg) was added to 1 ml of phosphate buffered saline (PBS, pH 7.4) and incubated at 37° C. on a rotating platform (140 RPM). At selected time points, supernatant was collected and fresh PBS added. DXR-conjugate concentration was measured by absorbance at 480 nm.

Results

Rod-shaped of DXR-PSA-PEG$_3$, were produced with three different drug loading levels, 10%, 30%, and 50%. The DXR-PSA-PEG$_3$ conjugates were formed into rods with a diameter of 0.5 mm, a length of 0.5 cm, and a mass of 1 mg.

Figure 8:
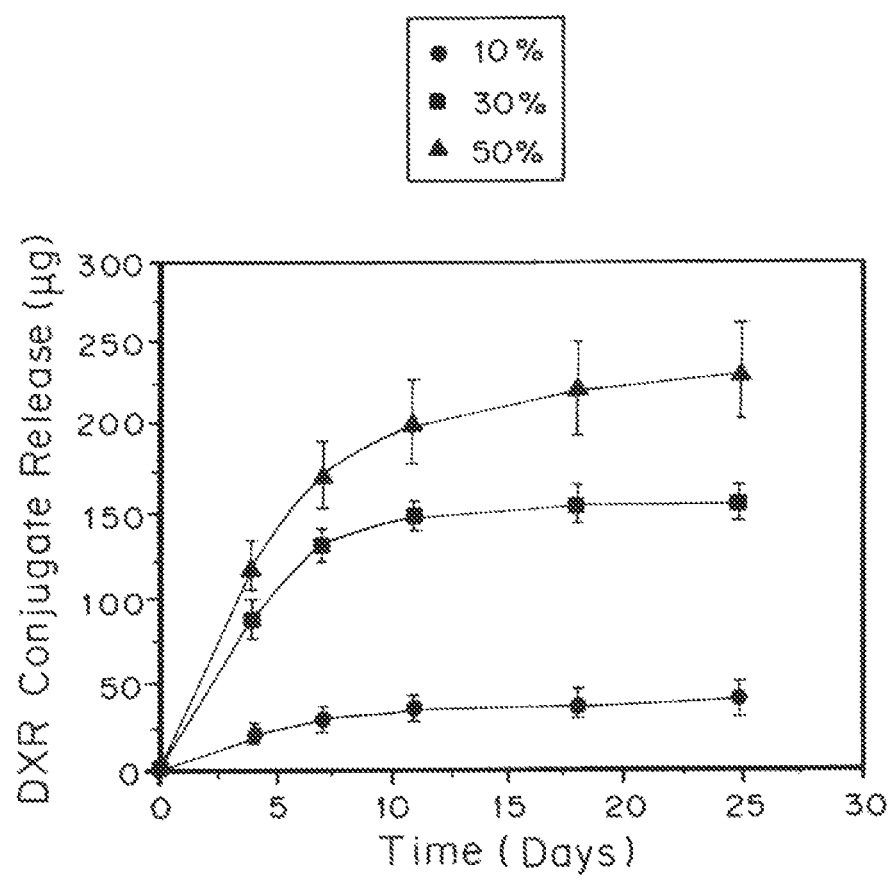
FIG. 8 is a graph showing release of doxorubicin (DXR) conjugate in vitro (µg) as a function of time (days) for polymer rods containing 10% DXR (●), 30% DXR (■) and 50% DXR (▲).

The duration of in vitro drug release was evaluated using the of DXR-PSA-PEG$_3$ rods, with drug loading levels of 10%, 30%, and 50% (FIG. 8). Drug release from all three rods was sustained for at least 25 days.

These data demonstrate that the synthesis of rod-shaped DXR-PSA-PEG$_3$ conjugates is possible. Rods composed of DXR-PSA-PEG$_3$ conjugates with different drug concentrations were successfully synthesized, and all rods displayed sustained drug release in vitro. These data also suggest that rods of differing sizes, mass, and drug content can be produced and drug release rates optimized to obtain the most efficacious drug delivery profile for each delivered drug and for each therapeutic indication.

Example 5: Production of DXR-PCPH-PSA-PEG$_3$ Polymer Conjugates

Microparticles composed of a fully biodegradable DXR-PSA-PCPH-PEG$_3$ polymer drug conjugate were synthesized and displayed a slower drug release rate and more sustained drug release duration compared to the DXR-PSA-PEG$_3$ microparticles. The addition of CPH to the polymer increased the hydrophobicity of polymer-drug conjugate which resulted in a prolonged the duration of drug release, presumably due to a reduction in DXR solubility.

Materials and Methods

Synthesis of 1,6-bis(p-carboxyphenoxy)hexane (CPH)

1,6-bis(p-carboxyphenoxy)hexane (CPH) was synthesized as described by Conix (1966). Briefly, p-hydroxybenzoic acid (27.6 g) and sodium hydroxide (16.0 g) in water (80 mL) were stirred and heated to reflux temperature. 1,6-dibromohexane (96%, 15.7 mL) was added over a period of 30 min while maintaining at reflux temperature and refluxed for an additional 3.5 hours. Sodium hydroxide (4.0 g) dissolved in water (10 mL) was added to the mixture and refluxed for another 2 hours before allowing the reaction mixture to stand overnight at room temperature. The disodium salt was isolated by filtration, washed with 40 mL of methanol, and dissolved in distilled water. The solution was warmed to 60-70° C. and acidified with 6 N sulfuric acid. The dibasic acid was isolated by filtration and dried to constant weight under vacuum.

Synthesis of PreCPH 1,6-bis(p-carboxyphenoxy)hexane (CPH) (10.0 g) was refluxed in 200 mL of acetic anhydride for 30 min under nitrogen, followed by removal of unreacted diacid by filtration and solvent by evaporation. The residue was recrystallized from dimethylformamide and ethyl ether, washed with dry ethyl ether, and dried to constant weight under vacuum.

Synthesis of PEG$_3$-PSA-PCPH Prepolymer (Polyethylene glycol)$_3$-co-poly(sebacic acid)co-poly (CPH) (PEG$_3$-SA-CPH) was synthesized by melt condensation. Briefly, sebacic acid was refluxed in acetic anhydride to form sebacic acid prepolymer (Acyl-SA). Polyethylene glycol (PEG$_3$) was prepared by mixing CH$_3$O-PEG-NH$_2$ (2.0 g), citric acid (26 g), dicyclohexylcarbodiimide (DCC; 83 mg) and 4-(dimethylamino)pyridine (DMAP, 4.0 mg) which were added to 10 mL methylene chloride, stirred overnight at room temperature, then precipitated and washed with ether, and dried under vacuum. Next, PEG$_3$ (10% w/v), acyl-SA (60% w/v), and preCPH (30% w/v), were polymerized at 180° C. for 30 minutes. Nitrogen gas was swept into the flask every 30 second for 15 minutes. Polymers were cooled to ambient temperature, dissolved in chloroform and precipitated into excess petroleum ether. The precipitate was collected by filtration and dried under vacuum to constant weight, to produce the PEG$_3$-PSA-PCPH prepolymer.

Preparation of DXR-PSA-PCPH-PEG$_3$ Microparticles

To prepare DXR-PSA-PCPH-PEG$_3$ microparticles, 200 mg PEG$_3$-PSA-PCPH was dissolved in 3 mL dichloromethane (DCM) and mixed with 40 mg doxorubicin hydrochloride (DXR) (NetQem LLC, Durham, N.C.) dissolved in 1.5 mL DMSO. Following incubation at 50° C. for 30 min, the mixture was homogenized in 100 mL of PVA at 3,000 rpm for 1 min. After stirring for 2 hr, particles were collected by centrifugation (9,000×g for 25 minutes) and washed thrice before lyophilization.

Particle Characterization

Particle size was determined using a Coulter Multisizer IV (Beckman-Coulter Inc., Fullerton, Calif.). Greater than 100,000 particles were sized for each batch of microparticles to determine the mean particle diameter.

In Vitro Drug Release

DXR-PSA-PCPH-PEG$_3$ microparticles (2 mg) were suspended in phosphate buffered saline (PBS, pH 7.4), and incubated at 37° C. on a rotating platform (140 RPM). At selected time points, supernatant was collected by centrifugation (13,500×g for 5 min) and particles were resuspended in fresh PBS. DXR-conjugate was measured by absorbance at 480 nm.

Results

DXR-PSA-PCPH-PEG$_3$ microparticles were synthesized and displayed a mean size of 24.3±8.7 um with a drug loading level of 13.9%.

Figure 9A:
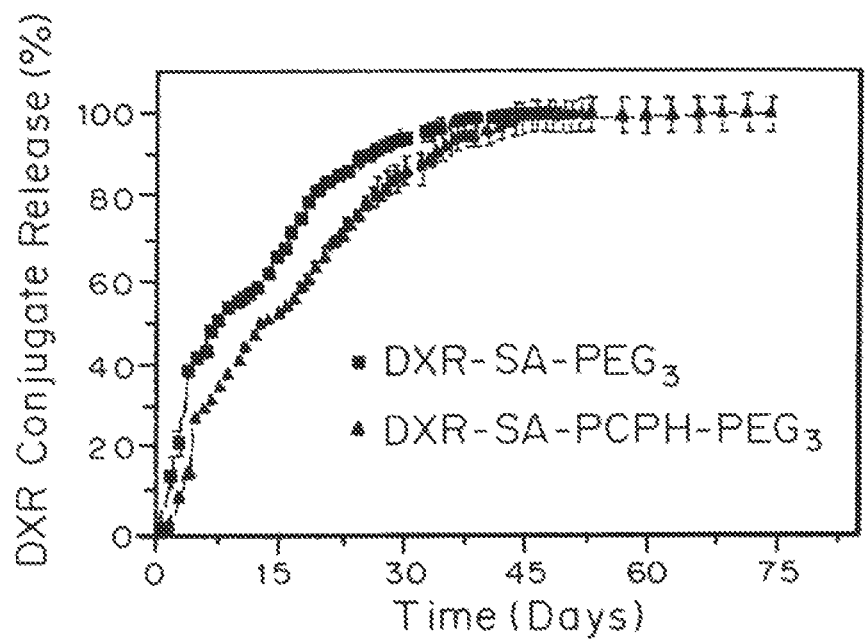
FIG. 9A is a graph showing the in vitro release profile of doxorubicin (DXR) conjugate from microparticles prepared from DXR-SA-PEG$_3$(■) and DXR-SA-CPH-PEG (▲).
Figure 9B:
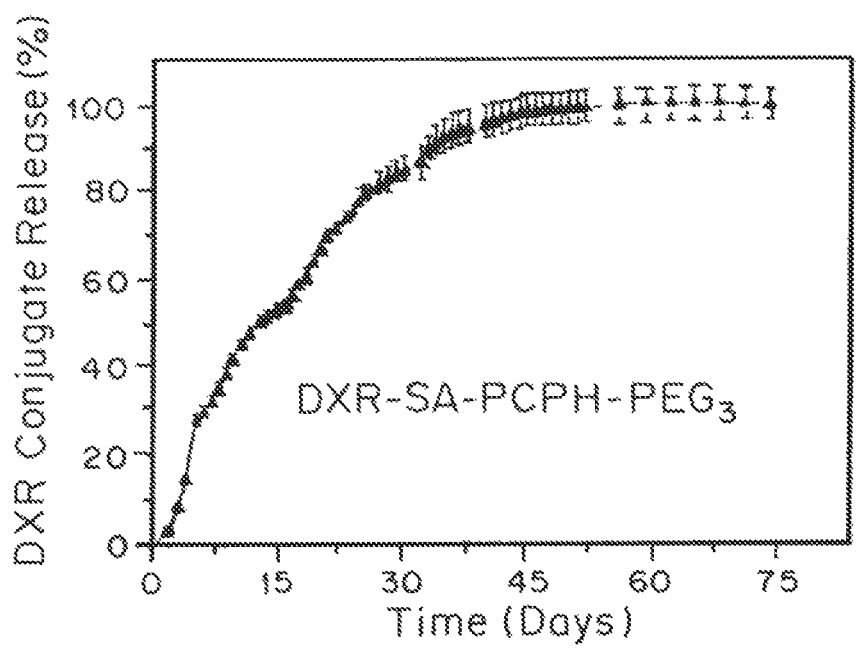
FIG. 9B is a graph showing the in vitro release profile of doxorubicin (DXR) conjugate from microparticles prepared from DXR-SA-CPH-PEG$_3$ (▲).

The duration of in vitro drug release was compared between the DXR-PSA-PCPH-PEG$_3$ microparticles and the DXR-PSA-PEG$_3$ microparticles (mean size 22.5+8.3 um). The DXR-PSA-PEG$_3$ microparticles showed drug release sustained for 45 days while the DXR-PSA-PCPH-PEG$_3$ microparticles demonstrated a slower drug release rate and drug release sustained for over 75 days (FIG. 9).

Microparticles composed of a fully biodegradable DXR-PSA-PCPH-PEG$_3$ polymer drug conjugate were synthesized. The DXR-PSA-PCPH-PEG$_3$ microparticles displayed a slower drug release rate and more sustained drug release duration compared to the DXR-PSA-PEG$_3$ microparticles, particles lacking the addition of the PCPH polymer. The addition of PCPH to the polymer increased the hydrophobicity of the released drug conjugate which is expected to reduce the solubility of DXR, and resulted in a prolonged duration of drug release.

These data demonstrate that by altering the polymer chemistry to increase the hydrophobicity of the released drug conjugate, the level and duration of drug release can be modified, suggesting that these parameters can be optimized to obtain the most efficacious drug delivery profile for each delivered drug and for each therapeutic indication.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. Micro- and/or nanoparticles formed of polymeric conjugates defined by one of the following formulae

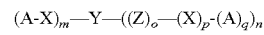

wherein

A represents, independently for each occurrence, a HIF-1 inhibitor;

X represents, independently for each occurrence, a hydrophobic polymer segment;

Y is absent, or represents a branch point;

Z represents, independently for each occurrence, a hydrophilic polymer segment; and o is 1;

p and q are independently 0 or 1;

m is an integer between one and twenty; and n is an integer between one and twenty.

2. The micro- and/or nanoparticles of claim 1, wherein A is an anthracycline.

3. The micro- and/or nanoparticles of claim 1, wherein Z is selected from the group consisting of a poly(alkylene glycol), a polysaccharide, poly(vinyl alcohol), polypyrrolidone, a polyoxyethylene block copolymer (PLURONIC®), and copolymers thereof.

4. The micro- and/or nanoparticles of claim 3, wherein Z for each occurrence comprises polyethylene glycol.

5. The micro- and/or nanoparticles of claim 1, wherein X is biodegradable.

6. The micro- and/or nanoparticles of claim 5, wherein X is selected from the group consisting of polyesters, polycaprolactone, polyanhydrides, and copolymers thereof.

7. The micro- and/or nanoparticles of claim 6, wherein X comprises a polyanhydride.

8. The micro- and/or nanoparticles of claim 7, wherein X comprises polysebacic anhydride.

9. The micro- and/or nanoparticles of claim 7, wherein X comprises 1,6 bis(p-carboxyphenoxy)hexane (CPH) or a combination of poly-CPH (PCPH) and polysebacic anhydride.

10. The micro- and/or nanoparticles of claim 1, wherein Y is from one of the following:

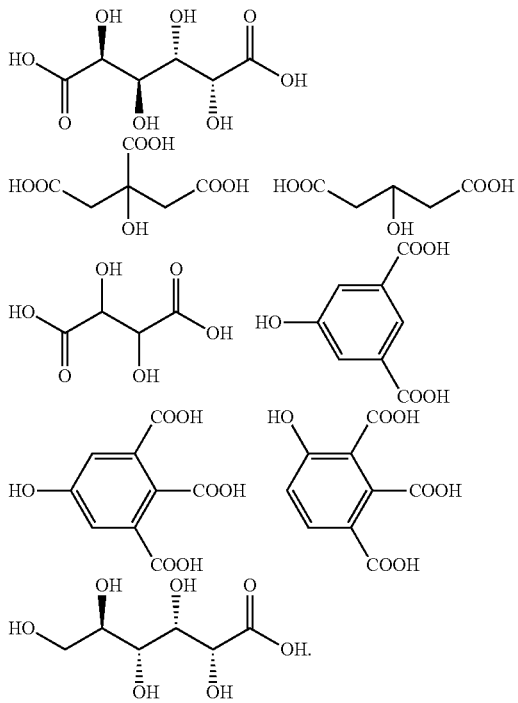

11. The micro- and/or nanoparticles of claim 10, wherein Y is from citric acid.

12. The micro- and/or nanoparticles of claim 1, defined by the following formula

wherein
A represents, independently for each occurrence, a HIF-1 inhibitor;
X represents, a hydrophobic polymer segment;
Y represents a branch point;
Z represents, independently for each occurrence, a hydrophilic polymer segment; and
n is an integer between one and ten or two and ten.

13. The micro- and/or nanoparticles of claim 12, wherein A is an anthracycline.

14. The micro- and/or nanoparticles of claim 12, wherein Z is selected from the group consisting of a poly(alkylene glycol), a polysaccharide, poly(vinyl alcohol), polypyrrolidone, a polyoxyethylene block copolymer, and copolymers thereof.

15. The micro- and/or nanoparticles of claim 14, wherein Z for each occurrence comprises polyethylene glycol.

16. The micro- and/or nanoparticles of claim 12, wherein X is biodegradable.

17. The micro- and/or nanoparticles of claim 16, wherein X is selected from the group consisting of polyesters, polycaprolactone, polyanhydrides, and copolymers thereof.

18. The micro- and/or nanoparticles of claim 17, wherein X comprises a polyanhydride.

19. The micro- and/or nanoparticles of claim 18, wherein X comprises polysebacic anhydride.

20. The micro- and/or nanoparticles of claim 17, wherein X comprises 1,6 bis(p-carboxyphenoxy)hexane (CPH) or a combination of CPH and polysebacic anhydride.

21. The micro- and/or nanoparticles of claim 12, wherein n is between 2 and 6.

22. The micro- and/or nanoparticles of claim 21, wherein n is 3.

23. The micro- and/or nanoparticles of claim 12, wherein Y is from one of the following:

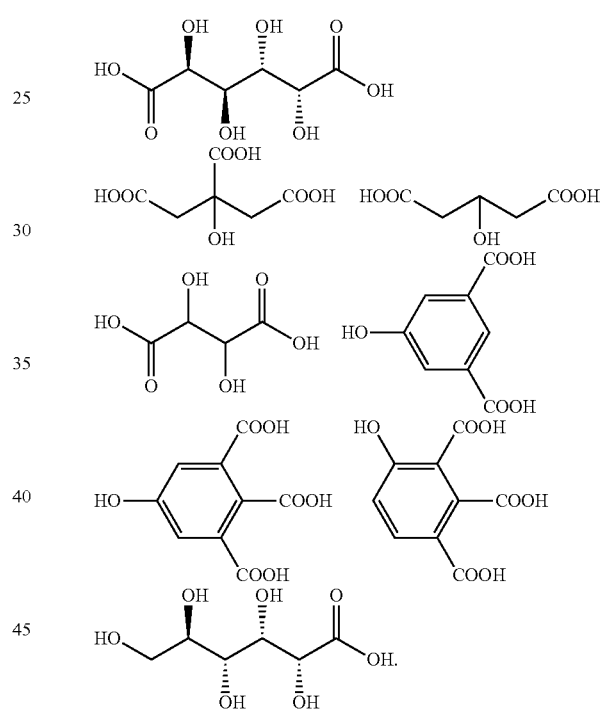

24. The micro- and/or nanoparticles of claim 23, wherein Y is from citric acid.

25. The micro- and/or nanoparticles of claim 1, wherein the polymeric conjugate is defined by Formula I

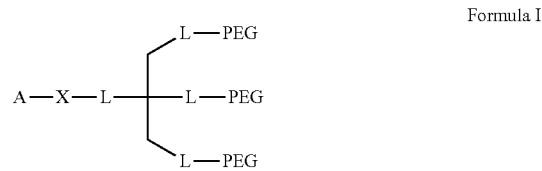

Formula I wherein
A is a HIF-1 inhibitor;
L represents, independently for each occurrence, an ether, thioether, secondary amine, tertiary amine, secondary amide, tertiary amide, secondary carbamate, tertiary carbamate, urea, sulfinyl group, or sulfonyl group;
PEG represents a polyethylene glycol chain; and
X represents a hydrophobic polymer segment.

26. The micro- and/or nanoparticles of claim 25, wherein X is biodegradable.

27. The micro- and/or nanoparticles of claim 25, wherein X is selected from the group consisting of polyesters, polycaprolactone, polyanhydrides, and copolymers thereof.

28. The micro- and/or nanoparticles of claim 27, wherein X comprises a polyanhydride.

29. The micro- and/or nanoparticles of claim 28, wherein X comprises polysebacic anhydride.

30. The micro- and/or nanoparticles of claim 26, wherein X comprises 1,6 bis(p-carboxyphenoxy)hexane (CPH) or a combination of CPH and polysebacic anhydride.

31. The micro- and/or nanoparticles of claim 25, wherein one or more of L are amides or esters.

32. The micro- and/or nanoparticles of claim 31, wherein A is an anthracycline.

33. The micro- and/or nanoparticles of claim 1, wherein the polymeric conjugate is defined by Formula IA

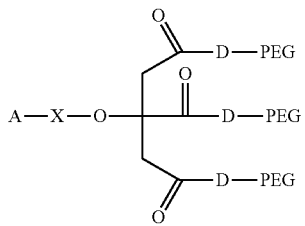

Formula IA wherein
A is a HIF-1 inhibitor;
D represents, independently for each occurrence, O or NH;
PEG represents a polyethylene glycol chain; and
X represents a hydrophobic polymer segment.

34. The micro- and/or nanoparticles of claim 33, wherein A is an anthracycline.

35. The micro- and/or nanoparticles of claim 33, wherein X is biodegradable.

36. The micro- and/or nanoparticles of claim 35, wherein X comprises a polyanhydride.

37. The micro- and/or nanoparticles of claim 36, wherein X comprises polysebacic anhydride.

38. The micro- and/or nanoparticles of claim 36, wherein X comprises 1,6 bis(p-carboxyphenoxy)hexane (CPH) or a combination of CPH and polysebacic anhydride.

39. A formulation comprising the micro- and/or nanoparticles of claim 1 in a pharmaceutically acceptable carrier.

40. A formulation comprising the micro- and/or nanoparticles of claim 12.

41. A formulation comprising the micro- and/or nanoparticles of claim 25.

42. The formulation of claim 39, comprising a conjugate defined by the following formula

A-X wherein
A is a HIF-1 inhibitor; and
X is a hydrophobic polymer segment.

43. The formulation of claim 42, wherein A is an anthracycline.

44. The formulation of claim 42, wherein X comprises a polyanhydride.

45. The formulation of claim 44, wherein X comprises polysebacic anhydride.

46. The conjugate of claim 44, wherein X comprises 1,6 bis(p-carboxyphenoxy)hexane (CPH) or a combination of CPH and polysebacic anhydride.

47. A method of treating a disease or disorder involving aberrant vascularization, comprising administering to a patient in need thereof the formulation of claim 39, in a pharmaceutically acceptable excipient.

48. A method of treating an intraocular neovascular disease or disorder of the eye comprising administering to the eye of a patient in need thereof the formulation of claim 39, in an excipient, pharmaceutically acceptable for administration to the eye.

49. The method of claim 48, wherein the intraocular neovascular disease or disorder is selected from the group consisting of age-related macular degeneration associated with choroidal neovascularization, proliferative diabetic retinopathy, proliferative vitreoretinopathy, retinopathy of prematurity, pathological myopia, von Hippel-Lindau disease, presumed ocular histoplasmosis syndrome (POHS), branch retinal vein occlusion, central retinal vein occlusion, branch retinal artery occlusion, central retinal artery occlusion, neovascularization associated with a tumor, neovascularization associated with an ocular wound, retinal neovascularization, corneal graft rejection, complications from surgery that cause neovascularization, complications from injury that cause neovascularization, and combinations thereof.

50. The method of claim 49, wherein the disease or disorder is wet age-related macular degeneration.

51. The method of claim 49, wherein the disease or disorder involves choroidal neovascularization.

52. The method of claim 51, wherein the formulation provides an effective amount of one or more HIF-1 inhibitors to decrease the area of choroidal neovascularization, as measured by fluorescein angiography, by at least 15%.

53. The method of claim 49, wherein the disease or disorder involves retinal neovascularization.

54. The method of claim 53, wherein the formulation provides an effective amount of one or more HIF-1 inhibitors to decrease the area of retinal neovascularization, as measured by fluorescein angiography, by at least 15%.

* * * * *

UNITED STATES PATENT AND TRADEMARK OFFICE
CERTIFICATE OF CORRECTION

PATENT NO. : 9,950,072 B2
APPLICATION NO. : 14/599853
DATED : April 24, 2018
INVENTOR(S) : Justin Scot Hanes, Peter A. Campochiaro and Jie Fu Page 1 of 1

It is certified that error appears in the above-identified patent and that said Letters Patent is hereby corrected as shown below:

In the Specification

Column 1, Lines 18-24, replace "This invention was made with Government Support under Agreements R01CA140746, P30EY001765, and U54CA151838 awarded to Justin Scot Hanes by the National Institutes of Health, and under agreement R01EY012609 awarded to Peter Anthony Campochiaro by the National Institutes of Health. The Government has certain rights in the invention." with --This invention was made with government support under CA140746, EY001765, CA151838, and EY012609 awarded by the National Institutes of Health. The government has certain right in the invention.--

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*